United States Patent
Mataki et al.

(10) Patent No.: US 7,695,641 B2
(45) Date of Patent: Apr. 13, 2010

(54) ORGANIC/INORGANIC COMPOSITE

(75) Inventors: Hiroshi Mataki, Kyoto (JP); Toshimi Fukui, Kyoto (JP)

(73) Assignee: KRI, Inc., Kyoto-shi, Kyoto (JP)

( * ) Notice: Subject to any disclaimer, the term of this patent is extended or adjusted under 35 U.S.C. 154(b) by 575 days.

(21) Appl. No.: 11/631,420

(22) PCT Filed: Jun. 30, 2005

(86) PCT No.: PCT/JP2005/012617

§ 371 (c)(1), (2), (4) Date: Jan. 3, 2007

(87) PCT Pub. No.: WO2006/004187

PCT Pub. Date: Jan. 12, 2006

(65) Prior Publication Data

US 2008/0287583 A1    Nov. 20, 2008

(30) Foreign Application Priority Data

Jul. 5, 2004 (JP) ............................. 2004-197711
Feb. 14, 2005 (JP) ............................. 2005-036985

(51) Int. Cl.
*H01B 1/08* (2006.01)
*C09K 11/02* (2006.01)
*H01S 3/00* (2006.01)

(52) U.S. Cl. ................. 252/301.4 F; 252/519.2; 359/333; 359/342

(58) Field of Classification Search .............. 252/519.2, 252/301.16, 301.4 F; 556/113, 146; 546/5; 362/84; 250/483.1; 359/333, 342
See application file for complete search history.

(56) References Cited

U.S. PATENT DOCUMENTS 4,106,857 A    8/1978  Snitzer
5,096,942 A *  3/1992  Long et al. .................. 523/212
5,134,107 A    7/1992  Narula (Continued)

FOREIGN PATENT DOCUMENTS

JP    A-05-088026    4/1993

(Continued)

OTHER PUBLICATIONS

Yasuchika Hasegawa, et al., "Enhanced Luminescence of Lanthanide (III) Complexes in Polymer Matrices," *Chemistry Letters*, (1999), pp. 35-36 (discussed on p. 9 and 18 of specification).

(Continued)

*Primary Examiner*—Mark Kopec
(74) *Attorney, Agent, or Firm*—Posz Law Group, PLC

(57) ABSTRACT

The present invention provides an organic/inorganic composite containing a rare earth metal or/and Period IV transition metal in which the aforementioned rare earth metal or/and Period IV transition metal is doped at a high concentration, and control of quenching and optical transparency are assured thereby; and an optical amplifier, a light control optical element, and luminescent device utilizing the same. The organic/inorganic composite containing a rare earth metal or/and Period IV transition metal is one in which at least one species of rare earth metal or/and Period IV transition metal is dispersed in an organic polymer, with the aforementioned composite containing an optically transparent organic polymer and an inorganic dispersion phase comprising: (1) a rare earth metal and (2) another element coordinated thereto via an oxygen atom(s). The inorganic dispersion phase in which another metal coordinates to rare earth metal or/and Period IV transition metal via an oxygen atom(s) preferably has an average particle size ranging from 0.1 to 1000 nm. Preferably, the ratio of rare earth metal or/and Period IV transition metal when mathematically converted to solid content is 90 mass % or less of the total mass of the organic polymer and the rare earth metal dispersion phase.

8 Claims, 9 Drawing Sheets

U.S. PATENT DOCUMENTS

| | | | |
|---|---|---|---|
| 5,252,740 A * | 10/1993 | Hale et al. ............ 546/263 |
| 5,961,208 A | 10/1999 | Karpen |
| 6,292,292 B1 | 9/2001 | Garito et al. |
| 6,416,867 B1 | 7/2002 | Karpen |
| 6,538,805 B1 | 3/2003 | Norwood et al. |
| 6,555,022 B2 | 4/2003 | Hampden-Smith et al. |
| 6,604,824 B2 | 8/2003 | Larson |
| 6,656,588 B1 | 12/2003 | Laine et al. |
| 6,656,608 B1 | 12/2003 | Kita et al. |
| 6,751,396 B2 | 6/2004 | Erben |
| 6,846,565 B2 | 1/2005 | Korgel et al. |
| 7,094,361 B2 | 8/2006 | Riman et al. |
| 7,229,600 B2 | 6/2007 | Yadav |
| 7,433,118 B2 | 10/2008 | Taylor-Smith |
| 2004/0004209 A1* | 1/2004 | Matsuba et al. ......... 252/518.1 |
| 2004/0156986 A1 | 8/2004 | Yadav |
| 2005/0151119 A1 | 7/2005 | Jones et al. |
| 2009/0131703 A1* | 5/2009 | Jhung et al. ............ 556/44 |

FOREIGN PATENT DOCUMENTS

| | | |
|---|---|---|
| JP | A-05-179147 | 7/1993 |
| JP | A-H07-324142 | 12/1995 |
| JP | A-08-301632 | 11/1996 |
| JP | A-10-036835 | 2/1998 |
| JP | A-H11-500584 | 1/1999 |
| JP | A-11-133227 | 5/1999 |
| JP | A-2000-208851 | 7/2000 |
| JP | A-2000-247986 | 9/2000 |
| JP | A-2000-256251 | 9/2000 |
| JP | A-2003-004930 | 1/2003 |
| JP | A-2002-507630 | 3/2003 |
| JP | A-2003-81983 | 3/2003 |
| JP | A-2003-081986 | 3/2003 |
| JP | A-2003-089756 | 3/2003 |
| JP | A-2003-147346 | 5/2003 |
| JP | A-2004-161849 | 6/2004 |
| JP | A-2004-226913 | 8/2004 |
| JP | A-2004-307853 | 11/2004 |
| JP | A-2005-76002 | 3/2005 |
| WO | WO 98/55885 A1 | 12/1998 |

OTHER PUBLICATIONS

Yasuchika Hasegawa, "How to Enhance the Luminescence of Neodymium (III) in Organic Media—Molecular Designs for Lanthanide (III) Luminescent Materials- ," *Chemistry and Industry*, (2000), vol. 53, No. 2, pp. 126-130 (Partial English translation provided) (discussed on p. 9 and 19 of specification).

J. Stouwdam, et al., "Lanthanide-Doped Nanoparticles with Excellent Luminescent Properties in Organic Media," *Chem. Mater.*, Oct. 31, 2003, pp. 4604-4616.

L. Beecroft, et al., "Nanocomposite Materials for Optical Applications," *Chem. Mater.*,1997, pp. 1302-1317.

P. Etienne, et al., "Active erbium-doped organic-inorganic waveguide," *Optics Communications* 174, Feb. 1, 2000, pp. 413-418.

* cited by examiner (a)   (b)

(a)

(b)

(c)

ORGANIC/INORGANIC COMPOSITE

TECHNICAL FIELD

The present invention relates to an organic/inorganic composite that is a composite of a rare earth metal or/and a Period IV transition metal and an organic polymer to be used in fields involving optical function applications wherein the transmission, refraction, reflection, polarization plane rotation, and the like of incident light are controlled, and functions such as luminescence (fluorescence) due to excitation by incident light, amplification, and the like are expressed. In addition, the present invention relates to an optical amplifier utilizing the aforementioned organic/inorganic composite wherein the intensity of light of a specific wavelength or bandwidth (optical signal) is amplified by light having a different wavelength or bandwidth (excitation light); a light control optical element utilizing the aforementioned organic/inorganic composite wherein the transmission, refraction, focusing, scattering, and the like of light are controlled, while the transmission or absorption of a specific wavelength or bandwidth is also controlled; and a luminescent device utilizing the aforementioned organic/inorganic composite wherein electric energy is converted to light energy.

BACKGROUND ART

Among the elements listed in the Periodic Table of the Elements, the following are collectively called rare earth metals or rare earth elements: scandium, yttrium, lanthanum, cerium, praseodymium, neodymium, promethium, samarium, europium, gadolinium, terbium, dysprosium, holmium, erbium, thulium, ytterbium, and lutetium. The first practical application of a rare earth metal was the gas mantle invented in the end of the 19th Century wherein cerium was mixed into the luminescence material of a gas lamp, which was five-times brighter than conventional gas lamps. Ever since, the rare earth metals have become indispensable materials in various fields involving optical function applications such as the following: red light fluorescent material in television cathode-ray tubes (europium, yttrium), x-ray CT scintillators in medical diagnosis (gadolinium, praseodymium), light control glasses (neodymium, cerium), solid-state lasers (yttrium, neodymium), electrostatic capacitors (yttrium, gadolinium); optical fiber amplifier (erbium, praseodymium, terbium, dysprosium), and magneto-optical recording disks (terbium, gadolinium). (For a general review, see Yasuo Suzuki, "Kidorui no Hanashi" [The Story of Rare Earth Elements], Shokabo Publishing Co., Ltd. 1998.) On the other hand, Period IV transition metals have been used in a similar manner as fluorescent materials in fluorescent lamps, mercury lamps, and cathode ray tubes. Moreover, because of their absorption properties, the transition metals have been used as various types of inorganic pigments, and they have often been used as magnetic materials as well.

The rare earth metals or/and Period IV transition metals have most often been used for doping in the form of rare earth metal ions or/and Period IV transition metal ions or rare earth metal oxides or/and Period IV transition metal oxides in a host material. Such host materials include glasses, garnet crystals, and transparent ceramic materials (zirconia and the like). However, all such host materials are inorganic, and there have been almost no examples wherein an organic material has been used as a host material.

For example, as an example of a light control optical element, a color filter multicolor correction lens utilizing absorption and the like have been studied.

Japanese Patent Application Laid-open No. H 11-133227 discloses a process for producing color filter wherein an inorganic pigment is formed into a substrate together with low melting glass frit and then enameled. A simpler means is a method wherein a pigment is mixed directly with an organic medium, and Japanese Patent Application Laid-open No. 2003-4930 and Japanese Patent Application Laid-open No. 2004-307853 disclose that a color filter having the required color and transmission characteristics can be obtained through the use of pigment fine particles of 100 nm or less in diameter. Although the pigment fine particles are needed to be dispersed in the organic medium in these means, they can hardly be dispersed without aggregation, which could lower the optical properties such as transmittance, haze, and the like.

As a means of solving the above problems, Japanese Patent Application Laid-open No. 2004-226913 discloses that the uniform mixing of the (meth) acrylic acid salt of a rare earth metal with an acrylic monomer is effective for obtaining color correction and the like and a required color. However, in that method it is necessary to use an acrylic monomer as the organic polymer of the matrix material, and it is impossible to form a composite of colorants in a wide range of organic matrix materials.

In addition, if used as a luminescence material, when doping is performed with a rare earth metal or/and Period IV transition metal at a high concentration in an inorganic material, the rare earth metal or/and Period IV metal ingredients aggregate or markedly get closer to each other. As a result, such a process has a problem that it is difficult to dope at a high concentration because the phenomenon known as "quenching" occurs wherein the luminescence (fluorescence) is diminished, and essentially, only a maximum concentration of about 100 ppm of rare earth metal or/and Period IV transition metal can be attained in practice.

On the other hand, organic materials, organic polymers in particular, have excellent properties in terms of processability, light weight, cost effectiveness and the like, and they have become key materials sustaining modern society. Especially in fields involving optical function applications, which are the fields to which the present invention is closely related, organic polymers are widely used for plastic lenses in applications such as eyeglasses, contact lenses and the like (acrylic resin, polycarbonate, cyclic olefin resin and the like), optical disks (polycarbonate), plastic optical fibers (acrylic resin), and the like (see Fumio Ide, "Oputoerekutoronikusu to Kobunshi Zairyo" [Optoelectronics and Polymer Materials], Kyoritsu Shuppan Co., Ltd. 1995). In addition to the doping into inorganic materials such as glasses, garnet crystals, ceramics and the like, the doping of rare earth metals or/and Period IV transition metals, that are used in various fields involving optical function application, into organic materials, especially organic polymers, makes it possible to bring about novel uses that provide better performance than inorganic materials with respect to processability, light weight, cost effectiveness, and the like.

However, there has been a problem that it has been impossible to manufacture materials wherein an organic polymer as a host material is doped with a rare earth metal or/and Period IV transition metal because rare earth metals or/and Period IV transition metals are hardly dispersible/soluble in an organic medium.

Optical amplifiers are the number one application wherein rare earth metals are used. As our advanced information society has become more widespread, the role of optical communications technology has become more important because the amount of data has become increasingly larger and data processing and transmission rates have become increasingly faster. Therefore, optical communications networks are being built not only as main lines in Japan but also on a global scale. In the 1990s the wavelength division multiplexing (WDM) transmission format wherein a plurality of optical signals with different wavelengths are transmitted simultaneously in a single optical fiber became commercialized, and the construction of large capacity high speed data communications networks was accelerated. One essential basic technology enabling the commercialization of such a WDM transmission format is optical amplification technology. In existing commercial optical amplification technology, an optical signal light in the 1550 nm bandwidth is excited by a semiconductor laser with a wavelength of 980 nm, 1480 nm, and the like. The optical fiber that carries the optical signal light and excitation light is doped with a rare earth metal, and after the rare earth metal is excited by the excitation light, the optical signal light that has become attenuated due to the long distance transmission process is supplemented by superimposing the light emitted by the rare earth metal in the 1550 nm band onto the optical signal light. Erbium is the most well-known rare earth metal that is doped into optical fibers, and the erbium-doped fiber amplifier (EDFA) is widely available for commercial use. In addition to erbium, the development of optical amplifiers using rare earth metals such as praseodymium, thulium and the like in accordance with the optical signal bandwidths used is proceeding vigorously.

In general, rare earth metals are doped in silica glass optical fibers at a concentration of 500 to 1000 ppm. When added at higher concentrations, the rare earth metal elements aggregate and a phenomenon occurs wherein the energy of a rare earth metal atom excited by the excitation light transfers to an adjacent rare earth metal atom before emission of the light corresponding to the optical signal wavelength, and thus the desired emission cannot be obtained. This is called "concentration quenching" and delineates the boundary wherein a rare earth metal can be doped into a silica glass optical fiber. As a result, in practice an optical fiber approximately 100 m long is needed to amplify an optical signal to the practically requisite intensity using excitation light, and this is a factor limiting the miniaturization of optical amplifiers (see Shoichi Sudo, ed., "Erubiumu Tenka Hikari Faiba Zofukuki" [Erbium-added Fiber optic Amplifiers], The Optronics Co., Ltd., 1999, p. 50).

With respect to such optical amplifiers, studies are underway in which, as various types of glass lenses have been replaced by organic polymer molded lenses, conversion of a silica glass matrix material to an organic polymer matrix material is attempted to make low-cost optical amplifiers practical and increase their cost effectiveness, which will be necessary not only for long distance main line fiber optic networks, but also for the massive fiber optic transmission lines of subscriber systems and the like that are becoming more widespread in average households (see Japanese Patent Application Laid-open No. H05-088026, Japanese Patent Application Laid-open No. 2000-208851, U.S. Pat. No. 6,292,292, U.S. Pat. No. 6,538,805, U.S. Pat. No. 6,751,396, Japanese Patent Application Laid-open No. 2000-256251, and Japanese Patent Application Laid-open No. H05-179147).

There is a problem, however, because rare earth metals do not easily dissolve or disperse in an organic medium. As a result, it has been impossible to dope a rare earth metal into an organic polymer matrix material, which provides excellent cost effectiveness in plastic optical fibers and the like, and this makes it difficult to improve greater cost effectiveness in optical transmission networks by the practical application of a low cost optical amplifier.

In general, fluorescent materials contain rare earth metals that can be listed as rare earth metals usable for doping organic polymers. Such fluorescent materials comprise three components, i.e., a host material, an activator, and a coactivator. Crystals of oxides and crystals of ionic compounds are used as the host material (see M. T. Anderson, et al., "Phosphors for Flat Panel Emission Displays," in B. G. Potter, Jr. et al., eds. Synthesis and Application of Lanthanide-Doped Materials, p. 79, The American Ceramic Society 1996). In other words, the goal has been achieved not by directly doping an organic polymer with a rare earth metal having fluorescence itself as the activator, but by first doping oxide crystals such as yttrium-aluminum-garnet (YAG) and the like with a rare earth metal, and then pulverizing the crystals and mixing them with an organic polymer. However, when such means are used, baking at a high temperature of about 1400° C. is necessary to form the YAG crystals, which increases the processing cost. In addition, the particle size of the pulverized fluorescent materials containing the rare earth metal are generally 1000 nm (1 μm) or more, and when they are dispersed at a high concentration for the purpose of using them in an optical amplifier, transparency is decreased due to optical scattering, and the product can no longer function as an optical waveguide. Thus, there is a concentration limitation below which fluorescent materials, prepared by doping rare earth metals into a host material such as a crystal, can be dispersed in a resin, and it is impossible to achieve both the miniaturization of optical amplifiers by using a high concentration of doping agent and an improvement in cost effectiveness by using an organic material as an optical transmission medium.

As a method of using a host material containing a rare earth metal in the same way as a fluorescent material, a means wherein the rare earth metal is carried by fine particles (Japanese Patent Application Laid-open No. 2003-89756) and a means wherein the rare earth metal is embedded in fine particles by ion implantation (L. H. Slooff, et al., Journal of Applied Physics, Vol. 83, p. 497, 1998) have been proposed, but both involve the problem wherein optical transparency is hindered because of the large size of the fine particles.

On the other hand, as means for doping an organic polymer directly with a rare earth metal, a method for synthesizing an organic/inorganic composite has been proposed wherein (a) an organic coordination compound between a rare earth metal and an organic ligand such as a pyridine, phenanthrolene, quinoline, β-diketone or the like is formed initially, and the rare earth metal is dispersed in an organic polymer thereby; and (b) the rare earth metal is contained in an organic cage complexes, and the inclusion compound is dispersed in an organic polymer; and the like (see L. H. Slooff, et al., Journal of Applied Physics, Vol. 83, p. 497, 1998).

Such means illustrated by (a) and (b) above broaden the type of rare earth metal that can be used and the range of concentration. Moreover, the dispersion phase containing the rare earth metal obtained thereby has molecular order, so even though the dispersion phase may aggregate somewhat, the size can be limited to a range from roughly a few nanometers to about 20 nm, and this enables doping at a high concentration without causing the decrease in transparency that accompanies optical scattering. There is a problem, however, because when these means are used, the excited state energy in the rare earth metal that has been excited by the excitation light transfers to the molecular vibrations of the CH and OH groups in the organic cage complexes or/and organic ligands, that are directly bonded to the rare earth metal, in accordance with the Franck-Condon principle known from quantum mechanics, and the emission process specific to the rare earth metal is inhibited (quenched) thereby (see W. Siebrand, The Journal of Chemical Physics, Vol. 46, p. 440, 1967).

For solving such a problem, a means has been proposed wherein quenching is suppressed by insuring that the excitation energy level of the rare earth metal and the excitation energy level of the organic ligands or organic cage complexes do not overlap by either fluorinating or deuterating the CH groups of the organic ligands of the rare earth metal coordination compound or organic cage complexes (Y. Hasegawa, et al., Chemistry Letters, 1999, p. 35 and Hasegawa "Yuki Baitai Chu de Hikaranai Neodymium o Donoyouni Hikaraseruka?" [How can we make neodymium, which does not emit light in an organic medium, emit light?] Kagaku to Kogyo (Chemistry and Chemical Industry), Vol. 53, page 126, 2000). Such a means is effective in terms of suppressing quenching while enabling a rare earth metal to be dissolved or dispersed in an organic medium at a high concentration. However, the problem remains that the fluorides and deuterides used as a starting material are very expensive, and therefore such a means cannot bring about the effect of improving the cost effectiveness of optical transmission networks that can be expected to accompany the practical application of optical amplifiers having an organic polymer as a matrix material.

A light control optical element can be listed as a second application using a rare earth metal. Light can be sensed by human eyes via various optical elements that control the transmission, refraction, focusing, scattering and the like of light. Many kinds of optical elements can be listed such as the lenses used in eyeglasses, the covers and lighting windows used in various lighting devices, the optical filters used in television receivers, the windows and lenses used in goggles in industrial processes such as welding and in medical therapy, and so on. A variety of optical elements, not only limited to the examples described above, have the important function of controlling the transmission, refraction, focusing, scattering and the like of light in various kinds of optical instruments. Such optical elements generally have a high transparency in the visible wavelength range. However, many other optical elements are also used to control transmission or absorption of both natural and artificial light such as light control lenses, light control glasses, and the like, and, as a group, such elements are called light control optical elements.

Among the lenses for eyeglasses in the examples noted above, lenses for sunglasses, used for the reduction of sickening glare by decreasing light intensity, is the most typical example of a light control optical element. In particular, lenses for sunglasses with a high antiglare effect can be obtained by reducing the amount of light at wavelengths of 400 to 500 nm. As part of the discussion of lenses for eyeglasses, there are persons who have a visual disorder characterized by difficulty in distinguishing colors because they have a congenital visual sensitivity curve that is different from the visual sensitivity curve of normal persons, and for such persons there are corrective lenses that adjust the transmittance value of light to match the visual sensitivity of the person having the visual disorder by selectively amplifying the absorption of light at specific wavelengths. Among the lighting windows or covers listed above, windows and covers with a strong antiglare effect can be obtained for lights having halogen lamps such as those used in automobile headlights and the like by controlling the transmittance of a light at wavelengths of 560 to 600 nm.

Thus, means wherein a material forming an optical element is doped with various light absorbing materials such as pigments and the like are known as means for controlling the transmission or absorption of light of a specific wavelength or wavelength band. Among them, the elements listed above and generally called rare earth metals or rare earth elements or/and Period IV transition metals of vanadium, chromium, manganese, iron, cobalt, nickel and copper, are known to be excellent as doping materials for controlling the transmission or absorption of light of a specific wavelength or waveband in accordance with the use or required purpose, because each element presents a sharp and large absorption spectrum at a particular waveband. With respect to the inventions utilizing the features of these rare earth metals or/and Period IV transition metals, there are many applications such as the following: contrast reinforced glasses and a lens using the same wherein glass is doped with neodymium oxide (Nd2O3) (Japanese Patent Application Laid-open No. H08-301632, U.S. Pat. No. 6,604,824) and windows using the same (U.S. Pat. No. 6,416,867); automobile headlights (U.S. Pat. No. 5,961,208); an optical filter (U.S. Pat. No. 4,106,857) wherein glass is doped with various rare earth elements such as holmium, praseodymium, dysprosium, or the like.

On the other hand, as materials constituting various optical elements that control the transmission, refraction, focusing, and scattering of light and the like, polymer materials with excellent processability, cost effectiveness and light weight have become widespread, and have become indispensable materials technology for modern society, as in the field of light weight lenses for eyeglasses, lenses for optical disk devices and the like. Therefore, in the field of light control optical elements doped with a rare earth metal or/and Period IV transition metal such as those in the preceding paragraph are needed, there is a demand for such elements utilizing polymer materials.

However, rare earth metals or/and Period IV transition metals have the property of dissolving or dispersing very poorly in organic media, and therefore the practical application of light control optical elements having a polymer matrix material that express light transmission and absorption properties specific to rare earth elements has been inhibited thereby.

To resolve such a problem the following means for synthesizing an organic/inorganic composite have been proposed in the past: (a) a coordination compound between a rare earth metal or/and Period IV transition metal and an organic ligand such as a pyridine, phenanthrolene, quinoline, β-diketone or the like is initially formed, and then the rare earth metal or/and Period IV transition metal is dispersed in an organic polymer thereby; (b) a rare earth metal or/and Period IV transition metal is included in an organic cage complexes, and the inclusion compound is dispersed in an organic polymer; (c) a polymer is formed using a polymer synthesizing monomer of a rare earth metal or/and Period IV transition metal; and the like.

When methods (a) and (b) are used, however, absorption in the UV region due to the organic ligands or organic cage complexes tends to increase, and this induces an energy transfer from the organic ligands or organic cage complexes to the matrix material polymer, and UV light degradation of the matrix material polymer by the generation of radicals formed upon cleavage of the molecular chains in the organic ligands or organic cage complexes and the like. In addition, the cost of the starting materials of most such organic ligands or organic cage complexes is high, and the high cost effectiveness that is the feature of a polymer optical element is impaired.

As an example of method (c), a method is known wherein a (meth) acrylic acid rare earth metal salt, hydroxyalkyl (meth)acrylate and phthalic acid, and a monomer copolymerizable with these are mixed, and the mixture is polymerized to produce a polymer (see Japanese Patent Application Laid-open No. 2004-226913). There is a problem, however, because when this method is used, the polymer material that can be used as a matrix is limited to a very small number of polymers such as acrylic resins, styrene resins, and the like, and it is impossible to satisfy the need for polymeric optical elements wherein various polymer materials such as polycarbonate resins, cyclic olefin resins, polyester resins, epoxy resins and the like have been developed as a matrix.

A luminescent device can be listed as a third application using a rare earth metal. Ever since Edison invented the incandescent bulb in the end of the 19th Century, various electric lamps and discharge tubes represented by fluorescent lamps have made major contributions to life in society. In the 1960s, light emitting diodes (LEDs) comprising compound semiconductors such as gallium arsenide and the like became practical, and they became widespread as miniature light emitting elements of infrared light, red light, green light and the like. The optical device of the present invention is a device that converts electric energy to light energy, as typified by various electric bulbs, discharge tubes, LED devices and the like. More specifically, as shown in FIGS. 14(a) to 14(c), the electric energy is converted by a light emitting element to light energy, which in turn is reconverted to light at a wavelength suitable for the application thereof by a fluorescent material containing a rare earth metal that is excited by the light emitted from this light emitting element. Thus, even when the light emitting element itself is one wherein, for example, electric energy is converted to UV light, it becomes possible to obtain light of the various wavelengths peculiar to each of the rare earth metals because this UV light excites the fluorescent material containing the rare earth metal.

Generally speaking, an LED comprising a compound semiconductor such as gallium arsenide, gallium phosphide and the like is known to have a higher luminous efficiency (conversion efficiency from electric energy to light energy) than an incandescent electric bulb or discharge tubes. The emission of red light can be obtained from compound semiconductors such as gallium arsenide, gallium arsenide phosphide and the like; the emission of red to yellow light can be obtained from aluminum indium gallium phosphide; and the emission of green light can be obtained from gallium phosphide. These lights are used in light emitting indicators of various types of electronic equipment, light emitting elements for remote control devices that operate various electronic equipment, LED display modules, and the like. In addition, recently a blue LED has been realized by the invention of a gallium nitride LED, and full color, large screen displays integrating various LEDs emitting the three primary colors of red, green and blue have been put into practical uses. Thus, as LEDs have extensively used from a point light source to a flat panel light source, there arises a vigorous movement in which lights that heretofore have been dependent on incandescent bulbs and discharge tubes are replaced by LEDs. Especially, the use of LEDs, which have a conversion efficiency from electric energy to light energy much higher than that of glass tube incandescent bulbs and discharge tubes, is an effective means to promote energy savings today when the problem of global warming has become severe. In Japan, the technological development of the use of LEDs has been promoted by the "Project for the Development of Compound Semiconductors for High Efficiency Optoelectronic Conversion" (nicknamed: "Light of the 21st Century Project") established by the Ministry of Economy, Trade and Industry in 1998. In the course of such technical development a white LED has been developed, and LEDs are becoming more widespread as a light source for lamps in place of incandescent bulbs and discharge tubes.

There are three methods for obtaining a white LED: (1) Obtaining white as a mixed color by integrating red, green and blue LEDs; (2) Obtaining white as a mixed color of yellow and blue by generating blue light with a blue LED and simultaneously generating yellow fluorescent light by exciting a fluorescent material with the blue light; and (3) Obtaining white by exciting three types of fluorescent materials that emit red (R), green (G), and blue (B) using a blue LED or an ultraviolet LED, and then combining the three primary colors R, G, and B (Tsunemasa Taguchi, ed. "Hakushoku LED Shomei System no Kokido/Kokoritsu/Chojumyoka Gijutsu" [Technology for High Intensity/High Efficiency/Long Life White LED Lighting Systems] Gijutsu Joho Kyokai, 2003).

If method (1) is used, a drive circuit for each of the three colors must be provided because the operating characteristics of the LEDs corresponding to each of the three colors are different, and this will interfere with miniaturization, less power consumption and the like, and therefore methods (2) and (3) are considered more practical.

Incidentally, it is known that the background of achieving white light that is excellent in intensity and color rendering properties in various types of incandescent and discharge tubes was originated from the use of a rare earth metal as a luminescence material. It is said that the first practical application of a rare earth metal was the gas mantle invented in the end of the 19th Century wherein cerium was mixed into the luminescence material of a gas lamp, which was five-times brighter than conventional gas lamps, and rare earth metals such as cerium (Ce), neodymium (Nd), and europium (Eu) have come to be used in incandescent and discharge tubes. Therefore, even when methods (2) and (3) are used, it is preferable to use these rare earth metals as luminescence materials that are excited by blue light or UV light. However, for using a rare earth metal as a luminescence material, as shown in FIG. 14(c), the general construction of the LED must be sealed with a resin after the light emitting element 31 (in this case, an LED chip) is mounted on a substrate. If the desired rare earth metal 33 such as Ce, Tb, Eu and the like, which are luminescence materials, can be dispersed in the resin as shown in FIG. 14(c), white light can be obtained as a mixed color with the fluorescent light 34 emitted from the rare earth metal 33 that has been excited by the light 32 emitted from the LED. There is a problem, however, because the rare earth metal does not easily dissolve in an organic medium such as the LED sealing resin 35.

To overcome this kind of problem, a fluorescent material containing a rare earth metal has been used in the past in display applications such as television receivers, flat panel displays and the like, because it will disperse the rare earth metal uniformly in an organic medium such as the LED sealing resin 35 and the like. Such fluorescent materials comprise three components, i.e., a host material, an activator, and a co-activator. Crystals of oxides and crystals of ionic compounds are used as the host material (see M. T. Anderson, et al., "Phosphors for Flat Panel Emission Displays," in B. G. Potter, Jr. et al., eds. Synthesis and Application of Lanthanide-Doped Materials, p. 79, The American Ceramic Society 1996). In other words, the goal has been achieved not by directly doping an LED sealing resin with a rare earth metal itself, which is a luminescence material, but by first doping oxide crystals such as yttrium-aluminum-garnet (YAG) and the like with a rare earth metal, and then pulverizing the crystals and mixing them with a resin.

However, when such a means is used, baking at a high temperature of about 1400° C. is necessary to form the YAG crystals, which increases the processing cost. In addition, the particle size of the pulverized fluorescent material containing the rare earth metal generally has a lower limit ranging from 1000 nm (1 μm) to several hundred nanometers, and when the particles are dispersed at a high concentration, transparency is decreased due to optical scattering that cannot be ignored. Thus, there is a concentration limitation below which fluorescent materials, prepared by doping rare earth metals into a host material such as a crystal, can be dispersed in a resin, and it is impossible to vary the dispersion concentration freely over a wide range.

As means for solving such a problem originating in fluorescent materials that have been used in the past and doping an organic medium directly with a rare earth metal, an organic/inorganic composite synthesis means has been proposed wherein (a) a coordination compound between a rare earth metal and an organic ligand such as a pyridine, phenanthrolene, quinoline, β-diketone or the like is formed, and the rare earth metal is dispersed in an organic medium thereby; and (b) the rare earth metal is included in an organic cage complexes, and the inclusion compound is dispersed in an organic medium; and the like.

Such means illustrated by (a) and (b) above involve broadening the type of rare earth metal and the range of concentration limitations. There is a problem, however, because when these means are used, the excited state energy in the rare earth metal that has been excited by blue light transfers to the molecular vibrations of the CH and OH groups in the organic cage complexes and the organic ligand that is directly bonded to the rare earth metal due to the Franck-Condon principle known in quantum mechanics, and the emission process specific to the rare earth metal is inhibited (quenched) (see W. Siebrand, The Journal of Chemical Physics, Vol. 46, p. 440, 1967, and L. H. Slooff, et al., Journal of Applied Physics, Vol. 83, p. 497, 1998).

For solving such a problem, a means has been proposed wherein quenching is suppressed by insuring that the excitation energy level of the rare earth metal and the excitation energy level of the organic ligands or organic cage complexes do not overlap by either fluorinating or deuterating the CH groups of the organic ligand of the rare earth metal coordination compound or organic cage complexes (Japanese Patent Publication No. 10-36835, Japanese Patent Application Laid-open No. 2000-256251, Y. Hasegawa, et al., Chemistry Letters, 1999, p. 35 and Hasegawa "Yuki Baitai Chu de Hikaranai Neodymium o Donoyoni Hikaraseruka?" [How can we make neodymium, which does not emit light in an organic medium, emit light?] Kagaku to Kogyo (Chemistry and Chemical Industry) Vol. 53, page 126, 2000). Moreover, a luminescent device using a rare earth metal coordination compound obtained thereby has been proposed (Japanese Patent Application Laid-open No. 2003-81986, Japanese Patent Application Laid-open No. 2003-147346). Such a means is effective in terms of suppressing quenching while enabling a rare earth metal to be dissolved or dispersed in an organic medium at a high concentration. However, the problem remains that because the fluorides and deuterides used as a starting material are very expensive, such a means lacks the cost effectiveness required by LED illumination, and this prevents the same from becoming widespread as consumer appliances.

DISCLOSURE OF THE INVENTION

As noted above, an organic/inorganic composite wherein an organic polymer is doped by various methods with a rare earth metal or/and Period IV transition metal has been proposed. However, there is no known material that can manifest optical functions while satisfying all conditions of doping with a rare earth metal or/and Period IV transition metal at a high concentration, suppressing quenching, assuring optical transparency, and also assuring processability, light weight, and cost effectiveness that are the properties of a polymer-based optical element, and inhibiting the degradation of the polymeric matrix material caused by absorption in the UV range.

With the foregoing in view, an object of the present invention is to provide an organic/inorganic composite wherein doping at a high concentration is performed using a rare earth metal or/and Period IV transition metal, and both the requirements for suppressing quenching and assuring optical transparency are satisfied. A second object of the present invention is to provide an optical amplifier utilizing an organic/inorganic composite containing a rare earth metal, which make it possible (1) to dope rare earth metals at high concentrations, (2) to suppress quenching, (3) to assure high transparency, and (4) to improve cost effectiveness. A third object of the present invention is to provide a light control optical element used for controlling transmittance and absorbance of light at a specific wavelength or in specific wavelength region utilizing an organic/inorganic composite containing a rare earth metal or/and Period IV transition metal, which make it possible (1) to dope rare earth metals or/and Period IV transition metals at high concentrations, (2) to avoid UV-induced degradation of the polymer matrix, and (3) to assure excellent processability, light weight, and cost effectiveness. A fourth object of the present invention is to apply an organic/inorganic composite to a fluorescent material in a luminescent device that converts electric energy to light energy, which make it possible (1) to dope rare earth metal luminescence material at high concentrations, (2) to suppress quenching, (3) to assure optical transparency, and (4) to assure cost effectiveness. In particular, an object thereof is to provide a luminescent device having an LED with high luminous efficiency, color appearance, and excellent cost effectiveness as the light emitting element.

We performed diligent research to attain the above objects. As a result, we discovered that by coordinating a rare earth metal or/and Period IV transition metal with other metal(s) via an oxygen atom(s), not only can an organic polymer be doped with metal species at a high concentration, but also that quenching due to energy transfer between atoms of the rare earth metal or/and Period IV transition metal, and/or between atoms of the rare earth metal or/and Period IV transition metal and the CH and OH groups can be controlled thereby. In addition, we discovered that by controlling the diameters in the dispersion phase containing a rare earth metal or/and Period IV transition metal linked to other metal(s) via an oxygen atom(s), the optical transparency of a transparent organic polymer can be assured, thus completing the present invention. On the one hand, we discovered that by applying the organic/inorganic composite of the present invention, the aforementioned second object can be attained. More specifically, the optical amplifier of the present invention comprises an inorganic dispersion phase wherein a rare earth metal is coordinated to other metal(s) via an oxygen atom(s), and this inorganic dispersion phase is used by forming a composite thereof with an organic polymer. In addition, the inventors discovered that by applying the aforementioned organic/inorganic composite, the aforementioned third object can be attained. More specifically, the light control optical element of the present invention is a light control optical element which utilizes a rare earth metal or/and Period IV transition metal-containing organic/inorganic composite wherein an organic polymer is used to form a composite thereof with an inorganic dispersion phase, in which other metal(s) is (are) coordinated to a rare earth metal or/and Period IV transition metal via an oxygen atom(s). High concentration doping with the rare earth metal or/and Period IV transition metal is attainable thereby. Furthermore, even though the absorption of the rare earth metal or/and Period IV transition metal lies in the UV wavelength range, the excitation energy of the rare earth metal produced by absorption of UV light is not transferred to the polymeric matrix material via the ligand of the present invention wherein other metal(s) is (are) coordinated via an oxygen atom(s), and radical generation accompanied by the cleavage of the ligand itself does not occur. In addition, the starting materials required for working of the present invention are easily obtained and economically efficient, and because doping of the rare earth metal or/and Period IV transition metal in various polymeric matrix materials is enabled thereby, the cost effectiveness, processability and light weight, which are the features of a polymeric optical element, are not lost.

We also discovered that by applying the organic/inorganic composite of the present invention the aforementioned fourth object can be attained. More specifically, in the luminescent device of the present invention, the inorganic dispersion phase comprising a rare earth luminescence material wherein other metal(s) is (are) coordinated to a rare earth metal via an oxygen atom(s) is used by forming a composite thereof with an organic polymer.

In other words, the organic/inorganic composite of the present invention has the structure described below.

1. An organic/inorganic composite in which at least one species of rare earth metals or/and Period IV transition metals is dispersed in an organic polymer, the composite having an inorganic dispersion phase in which one or more other species of metals are coordinated to the at least one species of rare earth metals or/and Period IV transition metals via oxygen.

In accordance with the above constitution, high concentration doping in various organic polymers can be achieved by coordinating other metal(s) with a rare earth metal or/and Period IV transition metal via an oxygen atom(s), and specific absorption capability is imparted thereby to the organic polymer.

In addition, because the other metal(s) is (are) coordinated via an oxygen atom(s), quenching due to energy transfer between the rare earth metal and the CH and OH groups of the organic polymer is inhibited. Concurrently, the metal coordinated via an oxygen atom(s) suppresses quenching accompanied by proximity interactions, and/or cluster formation of the rare earth metal or/and Period IV transition metal. Applications of coordination compounds intended for the dispersion of a rare earth metal in an organic polymer are also described in the aforementioned prior art, and generally speaking, coordination to an organic compound is performed via an oxygen or nitrogen atom capable of coordination to a metal. However, quenching due to energy transfer between the rare earth metal and the CH and OH groups of the organic polymer noted above cannot be inhibited by coordination using an organic compound as a ligand. If coordination to the other metal(s) via an oxygen atom(s) is not performed, aggregation will occur among the atoms of the rare earth metal/and Period IV transition metal, and essentially dispersion in the organic polymer cannot occur. Even if dispersion at dilute concentrations were possible, it would be impossible to form a desired organic/inorganic composite containing a rare earth metal/and Period IV transition metal due to quenching accompanied by proximity interactions, and/or cluster formation among the atoms of the rare earth metal/and Period IV transition metal. In the present invention, the rare earth metal/and Period IV transition metal is coordinated via an oxygen atom(s) that is bonded to the other metal(s). The inorganic dispersion phase of the present invention is represented schematically in FIG. 1. As shown in the drawing, the rare earth metal/and Period IV transition metal-containing organic/inorganic composite of the present invention is formed by a composite containing an inorganic dispersion phase comprising a rare earth metal or/and Period IV transition metal 1 with which other metals 2 are coordinated thereto via an oxygen atom(s), and an organic polymer that is not shown in the drawing. What is important in the aforementioned inorganic dispersion phase is that the distance between the same species of rare earth metals/and Period IV transitions metals are kept to be apart by the ligands coordinated via oxygen atoms. Therefore, the number and type of ligands comprising oxygen and another metal are not fixed, and the present invention is not strictly limited stoichiometrically to the kind of molecular structure shown in FIG. 1.

When used as an optical material and the like, it is desirable that the organic polymer of the present invention have optical transparency (permeability). The transmittance value of the organic polymer is not particularly limited provided it is within a range having transparency, but a transmittance value of 30% to 100% is preferable, and a range of 80% to 100% is even more preferable. In addition, the rare earth metal/and Period IV transition metal-containing organic/inorganic composite of the present invention can take the form of an association structure provided that the distance between the same species of rare earth metals/and Period IV transition metals are kept to be apart.

In FIG. 1, R represents an alkyl group, alkylcarbonyl group such as an acetyl group and the like, or hydrogen and the like.

2. An organic/inorganic composite, which is an organic/inorganic composite having a rare earth metal/and Period IV transition metal, the organic/inorganic composite having an inorganic dispersion phase in which one or more other species of metals are coordinated to the rare earth metal/and Period IV transition metal via oxygen, the inorganic dispersion phase having an average particle diameter of 0.1 to 1000 nm.

In accordance with the above constitution, the average diameter of the rare earth metal/and Period IV transition metal dispersion phase in which other metal(s) is(are) coordinated to the aforementioned rare earth metal/and Period IV transition metal via an oxygen atom(s) lies within the aforementioned range, and excellent transparency of the organic/inorganic composite is assured thereby, because said diameter is relatively small in comparison with the wavelengths of light passing through the rare earth metal-containing organic/inorganic composite.

3. An organic/inorganic composite, wherein a proportion of a rare earth metal/and Period IV transition metal is 90 mass % or less, as calculated in terms of solid content, based on a total mass of an organic polymer and an inorganic dispersion phase in which other species of metals are coordinated to the rare earth metal/and Period IV transition metal via oxygen.

In accordance with the above constitution, a high level of optical transmission can be expressed in fields involving optical function applications with which the present invention is closely related, since there is no scattering loss of light due to secondary aggregation of the rare earth metal/and Period IV transition metal that is coordinated to other metal(s) via an oxygen atom(s). Thus, if the proportion of the rare earth metal/and Period IV transition metal, calculated as solids, is 90 mass % or less based on the total mass of the organic polymer and the inorganic dispersion phase comprising other metal(s) coordinated to the aforementioned rare earth metal/and Period IV transition metal via an oxygen atom(s), the object of the present invention can be attained, and the need will arise to control absorption of the wavelengths of light that pass through the organic/inorganic composite depending on the required use of the organic/inorganic composite obtained in the present invention. As a result, the proportion of the rare earth metal/and Period IV transition metal, calculated as solids, is preferably 30 mass % or less based on the total mass of the organic polymer and the inorganic dispersion phase comprising other metal(s) coordinated to the aforementioned rare earth metal/and Period IV transition metal via an oxygen atom(s).

4. An organic/inorganic composite, wherein a metal coordinated to a rare earth metal/and Period IV transition metal via oxygen is one or more species of elements selected from Group 3B, Group 4A, and Group 5A metals.

In accordance with the above constitution, coordination of the other metal(s) with the rare earth metal/and Period IV transition metal via an oxygen atom(s) will be facilitated, and effective dispersion into the organic polymer and effective suppression of quenching during the light emission process of the rare earth metal/and Period IV transition metal can be realized thereby.

5. An organic/inorganic composite, wherein an inorganic dispersion phase having a rare earth metal/and Period IV transition metal and other species of metals coordinated thereto via oxygen is prepared from a salt of the rare earth metal/and Period IV transition metal and an alkoxide of other species of metals.

In accordance with the above structure, the dispersion phase wherein the other metal(s) coordinates to the rare earth metal/and Period IV transition metal via an oxygen atom(s) can be formed efficiently.

As noted above, the organic/inorganic composite of the present invention has a structure comprising: a dispersion phase comprising a rare earth metal/and Period IV transition metal coordinated to other metal(s) via an oxygen atom(s); and an organic polymer. As a result, the present invention accomplishes the effect of providing an organic/inorganic composite wherein: a rare earth metal/and Period IV transition metal can be doped at a high concentration; color rendering properties dependent on the absorption of the doping metal are imparted in a state wherein optical transparency is assured; and quenching suppression and optical transparency are achieved.

6. An optical amplifier having an optical waveguide for transmitting light of a specific wavelength or waveband (signal light) and light having a different wavelength or waveband therefrom (excitation light), in which intensity of the signal light is amplified by the excitation light, wherein the optical waveguide is the organic/inorganic composite according to item 1.

In accordance with the above structure, high concentration doping of the rare earth metal in the organic polymer can be achieved by coordinating the rare earth metal with the other metals via an oxygen atom(s). In addition, by coordinating the other metals via an oxygen atom(s), quenching due to the energy transfer between the rare earth metal and the CH and OH groups of the organic polymer is suppressed. Concurrently, concentration quenching due to the proximity interactions or/and cluster formation of the rare earth metal is also suppressed thereby.

Use of a coordination compound for the purpose of dispersing rare earth metals in an organic polymer is described in the aforementioned prior art, and in general this prior art coordination to an organic compound is performed via an oxygen or nitrogen capable of coordination to a metal. However, the quenching due to energy transfer between the rare earth metal and the CH and OH groups of the organic polymer noted above cannot be controlled by coordination wherein an organic compound is used as a ligand.

If coordination with the other metals via an oxygen atom(s) is not performed, aggregation of the rare earth metals will occur, and essentially dispersion in the organic polymer cannot be achieved. Even if dispersion at dilute concentrations were possible, it would be impossible to form an organic/inorganic composite containing the intended rare earth metal due to quenching that accompanies proximity interactions and/or cluster formation among the atoms of the rare earth metal.

When used as an optical a material and the like, it is desirable that the organic polymer of the present invention have optical transparency (permeability). Although the transmittance of the organic polymer is not limited to a specific range provided that it is substantially transparent, a transmittance of 30% to 100% is preferable, and a range of 80% to 100% is even more preferable.

In addition, the inorganic dispersion phase containing a rare earth metal of the present invention can take the form of an association structure provided that the distance between the same species of rare earth metals are kept to be apart.

In the optical amplifier of the present invention, the average particle size of the inorganic dispersion phase as a whole wherein another metal is coordinated to a rare earth metal via an oxygen atom(s) preferably ranges from 0.1 to 1000 nm. Excellent transparency of the organic/inorganic composite containing a rare earth metal is assured thereby because the particle size is relatively small in comparison with the wavelength of light propagating in the organic/inorganic composite containing a rare earth metal.

In the optical amplifier of the present invention, the content of rare earth metals in terms of solid content is preferably 90 mass % or less of the total mass of the organic polymer and the inorganic dispersion phase wherein another metal is coordinated to the aforementioned rare earth metal via an oxygen atom(s). A high level of optical transmission can be expressed in fields involving optical function applications with which the present invention is closely related without bringing about scattering loss of light due to secondary aggregation of the rare earth metal that is coordinated to another metal via an oxygen atom(s). Thus, if the ratio of rare earth metal when mathematically converted to solid content is 90 mass % or less of the total mass of the organic polymer and the inorganic dispersion phase wherein another metal is coordinated to the aforementioned rare earth metal via an oxygen atom(s), the object of the present invention can be attained thereby, and because the need will arise to control absorption of the wavelength of light passing through the organic/inorganic composite containing a rare earth metal in accordance with the use of the organic/inorganic composite obtained in the present invention, the ratio of rare earth metal when mathematically converted to solid content is preferably 30 mass % or less of the total mass of the organic polymer and the inorganic dispersion phase wherein another metal is coordinated to the aforementioned rare earth metal via an oxygen atom(s).

In the optical amplifier of the present invention, the metal coordinated to the rare earth metal via an oxygen atom(s) is preferably one or more than one element selected from a group consisting of Group 3B, Group 4A, and Group 5A metals. Coordination of the other metal with the rare earth metal via an oxygen atom(s) will be facilitated thereby, and effective dispersion into the organic polymer and effective suppression of quenching during the light emission process of the rare earth metal can thus be realized.

In the optical amplifier of the present invention, the inorganic dispersion phase wherein a rare earth metal is coordinated to another metal via an oxygen atom(s) is preferably formed by a rare earth metal salt and an alkoxide of the other metal. In accordance with the above structure, the dispersion phase wherein the other metal coordinates with the rare earth metal via an oxygen atom(s) can be formed efficiently.

As noted above, the optical amplifier of the present invention has an optical waveguide wherein light of a specific wavelength or waveband (signal light) and light having a different wavelength or waveband therefrom (excitation light) is transferred thereby, and also has a structure comprising a dispersion phase containing a rare earth metal wherein another metal is coordinated to the rare earth metal via an oxygen atom(s); and an organic polymer.

As a result, the present invention: (1) enables high concentration doping of a rare earth metal (2) suppresses quenching and (3) can assure optical transparency. In addition, because the present invention does not require expensive starting materials such as fluorides and deuterides to control quenching and a high temperature process to form a host material such as oxide crystals and the like, it provides the effect of (4) realizing a assure of cost effectiveness.

7. A light control optical element having the organic/inorganic composite according to item 1.

In accordance with the above structure, high concentration doping of the organic polymer can be achieved by coordinating a rare earth metal or/and Period IV transition metal with another metal via an oxygen atom(s). In addition, because the other metal is coordinated via an oxygen atom(s), the present invention inhibits the energy transfer between the atoms of the rare earth metal and the CH and OH groups of the organic polymer.

With respect to the use of the coordination compound for the purpose of dispersing the rare earth metal or/and Period IV transition metal in the organic polymer, as described in the aforementioned prior art, generally speaking coordination with an organic compound is performed via an oxygen or nitrogen atom capable of coordination with a metal. However, energy transfer between the rare earth metal or/and Period IV transition metal and the CH and OH groups of the aforementioned organic polymer noted above cannot be inhibited by coordination using an organic compound as a ligand.

When used as an optical material and the like, it is desirable that the organic polymer of the present invention have optical transparency (permeability). The transmittance value of the organic polymer is not particularly limited provided it is within a range having transparency, but a transmittance value of 30% to 100% is preferable, and a range of 80% to 100% is even more preferable.

The light control optical element of the present invention may have a structure wherein the average particle size of the inorganic dispersion phase as a whole wherein another metal is coordinated thereto via an oxygen atom(s) ranges from 0.1 to 1000 nm.

In accordance with the above structure, the average particle size of the inorganic dispersion phase as a whole wherein another metal is coordinated to the aforementioned rare earth metal or/and Period IV transition metal via an oxygen atom(s) lies within the aforementioned range, and excellent transparency of the organic/inorganic composite is assured because the particle size is relatively small in comparison with the wavelength of light passing through the organic/inorganic composite containing a rare earth metal or/and Period IV transition metal.

The light control optical element of the present invention may have a structure wherein the ratio of rare earth metal or/and Period IV transition metal when mathematically converted to solid content is 90 mass % or less of the total mass of the organic polymer and the inorganic dispersion phase wherein another metal is coordinated to the aforementioned rare earth metal or/and Period IV transition metal via an oxygen atom(s).

In accordance with the above structure, a high level of optical transmission can be expressed in fields involving optical function applications with which the present invention is closely related without bringing about scattering loss of light due to secondary aggregation of the rare earth metal that is coordinated to another metal via an oxygen atom(s).

In the light control optical element of the present invention, the metal coordinated to the rare earth metal or/and Period IV transition metal via an oxygen atom(s) is preferably one or more than one element selected from a group consisting of Group 3B, Group 4A, and Group 5A metals.

In accordance with the above structure, coordination of the other metal with the rare earth metal via an oxygen atom(s) will be facilitated, and effective dispersion into the organic polymer can thus be realized thereby.

The light control optical element of the present invention may have a structure wherein the inorganic dispersion phase wherein a rare earth metal or/and Period IV transition metal is coordinated to another metal via an oxygen atom(s) is preferably formed by a rare earth metal salt and an alkoxide of the other metal.

In accordance with the above structure, the dispersion phase wherein the other metal coordinates with the rare earth metal or/and Period IV transition metal via an oxygen atom(s) can be formed efficiently.

The organic/inorganic composite containing a rare earth metal or/and a Period IV transition metal used in the light control optical element of the present invention has a structure comprising a dispersion phase containing a rare earth metal or/and Period IV transition metal wherein another metal is coordinated thereto via an oxygen atom(s); and an organic polymer.

As a result, the present invention accomplishes the effect of providing a light control optical element wherein: a rare earth metal is doped at a high concentration; and assurances of optical transparency and of transmission and absorption control of light a specific wavelength or waveband are achieved without inducing degradation of the polymeric matrix material accompanied by energy transfer of absorbed UV light and molecular chain cleavage.

8. A luminescent device having a light emitting element and an organic/inorganic composite in which a rare earth metal luminescence material emitting light when excited by light generated by the light emitting element is dispersed in an organic polymer, the organic/inorganic composite being the organic/inorganic composite according to item 1.

In accordance with the above structure, high concentration doping of the rare earth metal luminescence material in the organic polymer can be achieved by coordinating another metal with the rare earth metal via an oxygen atom(s). In addition, because the other metal is coordinated via an oxygen atom(s), quenching due to energy transfer between the rare earth metal and the CH and OH groups of the organic polymer is inhibited. Concurrently, quenching that accompanies proximity interactions or/and cluster formation between the metal coordinated via an oxygen atom(s) and the rare earth metal is also inhibited thereby.

Applications of coordination compounds intended for the dispersion of a rare earth metal in an organic polymer are also described in the aforementioned prior art, and in general prior art coordination with an organic compound is performed via an oxygen or nitrogen atom capable of coordination with a metal. However, the quenching due to energy transfer between the rare earth metal and the CH and OH groups of the organic polymer noted above cannot be inhibited by coordination wherein an organic compound is used as a ligand.

If coordination with the other metal via an oxygen atom(s) is not performed, aggregation will occur among the atoms of the rare earth metal, and essentially dispersion in the organic polymer cannot occur. Even if dispersion at dilute concentrations were possible, it would be impossible to form an organic/inorganic composite containing the intended rare earth metal due to quenching that accompanies proximity interactions or/and cluster formation among the atoms of the rare earth metal.

When used as an optical material and the like, it is desirable that the organic polymer of the luminescent device of the present invention have optical transparency (permeability). The transmittance value of the organic polymer is not particularly limited provided it is within a range having transparency, but a transmittance value of 30% to 100% is preferable, and a range of 80% to 100% is even more preferable.

The luminescent device of the present invention may have a structure wherein the light emitting element comprises a semiconductor wherein the main ingredients are a Group III element and Group V element of the Periodic Table, or a compound wherein the main ingredients are a Group II element and a Group IV element of the Periodic Table.

In accordance with the above structure, not only light having a wavelength in the visible bands, but also light of various wavelengths such as UV light and infrared light can be obtained. More specifically the conversion efficiency from electric energy to light energy of the aforementioned semiconductor is much higher than with an incandescent bulb or discharge tubes, and it is optimal for constructing a luminescent device featuring low power consumption and high intensity.

The luminescent device of the present invention may have a structure wherein the particle size of the inorganic dispersion phase as a whole wherein another metal is coordinated to the aforementioned rare earth metal via an oxygen atom(s) ranges from 0.1 to 1000 nm.

In accordance with the above structure, the average particle size of the rare earth metal dispersion phase wherein another metal is coordinated to the aforementioned rare earth metal via an oxygen atom(s) lies within the aforementioned range, and excellent transparency of the organic/inorganic composite is assured because the particle size is relatively small in comparison with the wavelengths of light passing through the organic/inorganic composite containing a rare earth metal.

The luminescent device of the present invention may have a structure wherein the ratio of rare earth metal when mathematically converted to solid content is 90 mass % or less of the total mass of the organic polymer and the inorganic dispersion phase wherein another metal is coordinated to the rare earth metal via an oxygen atom(s).

In accordance with the above structure, a high level of optical transmission can be expressed in fields involving optical function applications with which the present invention is closely related without bringing about scattering loss of light due to secondary aggregation of the rare earth metal that is coordinated to another metal via an oxygen atom(s). Thus, if the ratio of rare earth metal when mathematically converted to solid content is 90 mass % or less of the total mass of the organic polymer and the inorganic dispersion phase wherein another metal is coordinated thereto via an oxygen atom(s), the object of the present invention can be attained thereby, and because the need will arise to control absorption of the wavelength of light passing through the organic/inorganic composite containing a rare earth metal in accordance with the use of the organic/inorganic composite obtained in the present invention, the ratio of rare earth metal when mathematically converted to solid content is preferably 30 mass % or less of the total mass of the organic polymer and the inorganic dispersion phase wherein another metal is coordinated to the aforementioned rare earth metal via an oxygen atom(s).

The luminescent device of the present invention may have a structure wherein the metal coordinated to the rare earth metal via an oxygen atom(s) is one or more than one element selected from a group consisting of Group 3B, Group 4A, and Group 5A metals.

In accordance with the above structure, coordination between the rare earth metal with another metal via an oxygen atom(s) will be facilitated, and effective dispersion into the organic polymer and effective suppression of quenching during the light emission process of the rare earth metal can be realized thereby.

The luminescent device of the present invention may have a structure wherein the inorganic dispersion phase wherein a rare earth metal is coordinated to another metal via an oxygen atom(s) is formed by a rare earth metal salt and an alkoxide of the other metal.

In accordance with the above structure, a dispersion phase wherein another metal is coordinated to a rare earth metal is formed efficiently.

As noted above, the luminescent device of the present invention has a structure comprising: a light emitting element that converts electric energy to light energy; a rare earth metal luminescence material comprising an inorganic dispersion phase containing a rare earth metal wherein another metal is coordinated thereto via an oxygen atom(s); and an organic polymer.

As a result, the present invention: (1) enables high concentration doping of a rare earth metal (2) suppresses quenching and (3) can assure optical transparency. In addition, because the present invention does not require expensive starting materials such as fluorides and deuterides to suppress quenching and a high temperature process to form a host material such as oxide crystals and the like, it provides the effect of (4) realizing a assurance of cost effectiveness. In other words, an effect is realized in which a luminescent device is provided wherein a rare earth metal luminescence material is doped at a high concentration, suppression of quenching and optical transparency are assured, and cost effectiveness is excellent.

BRIEF DESCRIPTION OF THE DRAWINGS

FIG. 11($b$) is a schematic drawing showing the basic structure of an optical amplifier that is an optical waveguide amplifier;

FIG. 13($b$) is a drawing showing a typical light control optical element of the present invention;

FIG. 13($c$) is a drawing showing a typical light control optical element of the present invention;

FIG. 13($d$) is a drawing showing a typical light control optical element of the present invention;

FIG. 14($b$) is a schematic drawing of a discharge tube as an example of a luminescent device;

FIG. 14($c$) is a schematic drawing of an LED as an example of a luminescent device;

BEST MODE FOR CARRYING OUT THE INVENTION

Figure 1:
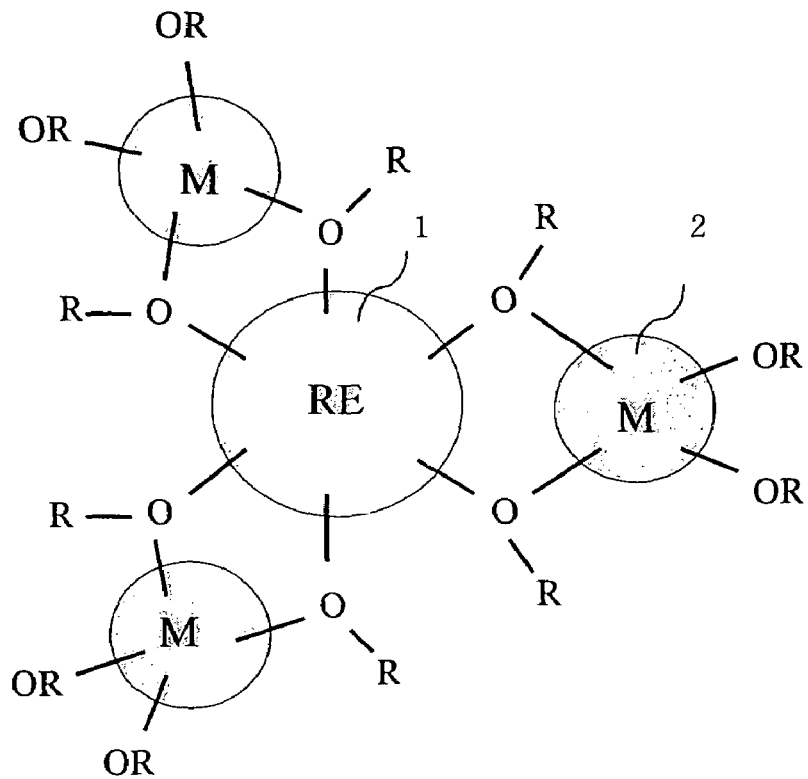
FIG. 1 is a schematic drawing of the inorganic dispersion phase wherein another metal is coordinated to a rare earth metal/and Period IV transition metal via an oxygen atom(s) among the organic/inorganic composites of the present invention.

The present invention is explained in greater detail below.

The organic/inorganic composite of the present invention is a composite of a rare earth metal/and a Period IV transition metal and an organic polymer to be used in fields involving optical function applications wherein the transmission, refraction, reflection, polarization plane rotation, and the like of incident light are controlled, and functions such as luminescence (fluorescence) due to excitation by incident light, amplification, and the like are expressed, said organic/inorganic composite comprising an inorganic dispersion phase (rare earth metal/and Period IV transition metal dispersion phase) wherein another metal coordinates thereto via an oxygen atom(s); and an organic polymer. In addition, the organic/inorganic composite of the present invention is a composite wherein at least one species of rare earth metal is dispersed in the organic polymer, and it may be an organic/inorganic composite containing a rare earth metal wherein another metal coordinates thereto via an oxygen atom(s).

The structure of the organic/inorganic composite of the present invention may be any combination of the following provided it contains a rare earth metal or/and Period IV transition metal; a metal capable of coordinating with the rare earth metal or/and Period IV transition metal via an oxygen atom(s); and an organic polymer. The method of forming the inorganic dispersion phase wherein another metal coordinates with the rare earth metal or/and Period IV transition metal via an oxygen atom(s) is not particularly limited, and it may be formed, for example, by a reaction between a rare earth metal salt/and Period IV transition metal salt and a metal alkoxide. The composite containing the inorganic dispersion phase wherein the rare earth metal/and Period IV transition metal is coordinated to another metal via an oxygen atom(s) can be prepared, for example, by mixing and dispersing an inorganic dispersion phase formed by a reaction between the aforementioned metal alkoxide and the rare earth metal salt/and Period IV transition metal salt together with an organic polymer.

[Rare Earth Metal] All of the following may be used as the rare earth metal: scandium, yttrium, lanthanum, cerium, praseodymium, neodymium, promethium, samarium, europium, gadolinium, terbium, dysprosium, holmium, erbium, thulium, ytterbium, and lutetium.

[Period IV Transition Metal] Vanadium, chromium, manganese, iron, cobalt, nickel, and copper are preferably used as the Period IV transition metal. A composite may be formed containing only one species, or two or more species of the rare earth metal and Period IV transition metal.

[Other Metal Coordinating with the Rare Earth Metal/and Period IV Transition Metal Via an Oxygen Atom(s)] The other metal is not particularly limited provided it is an element that can coordinate with a rare earth metal via an oxygen atom(s) and does not have an adverse effect on the required properties. Preferably, metals from Group 3B, Group 4A or Group 5A are used. More preferably, aluminum, gallium, titanium, zirconium, niobium, and tantalum are used.

[Preparation of Inorganic Dispersion Phase] The method of forming the inorganic dispersion phase is not particularly limited provided coordination bonding of the other metal with the intended rare earth species via an oxygen atom(s) is possible. The following methods, for example, are available: methods involving heat treatment and pulverization (when a metal salt, hydroxide, oxide, and the like is used as the starting material) after mixing the rare earth metal or/and Period IV transition metal starting material and the starting material of the metal capable of coordinating thereto; methods wherein the rare earth metal or/and Period IV transition metal and the metal capable of coordinating thereto are dissolved in a solvent, and then precipitated by hydrolysis; and methods wherein a rare earth metal salt/and Period IV transition metal salt is reacted with the alkoxide of the metal capable of coordinating thereto in an organic solvent.

To obtain a nanometer sized rare earth metal/and Period IV transition metal dispersion phase, the method wherein a rare earth metal salt/and Period IV transition metal salt is reacted with the alkoxide of a metal capable of coordinating thereto in an organic solvent is preferably used. The solvent to be used is not particularly limited, and any solvent may be used provided the ultimate reaction product that forms the coordination structure can be dispersed in the organic polymer. For example, a primary alcohol such as methanol, ethanol, 1-propanol, 2-propanol, 1-butanol, 2-butanol, t-butanol and the like; a polyhydric alcohol such as ethylene glycol, propylene glycol, glycerin, and the like; a glycol ether such as ethylene glycol monomethyl ether, ethylene glycol monoethyl ether, ethylene glycol monopropyl ether, propylene glycol-α-monomethyl ether, propylene glycol-α-monoethyl ether, and the like; a ketone such as acetone, methyl ethyl ketone, and the like; a cyclic ether such as tetrahydrofuran, dioxane, and the lie; an ester such as methyl acetate, ethyl acetate, propyl acetate and the like; acetonitrile; an aromatic compound such as benzene, toluene, xylene, and the like; and a hydrocarbon such as pentane, hexane, heptane, cyclohexane, and the like can be used as such a solvent. It is possible to use a method wherein heating to the reflux temperature of the solvent is performed to form the coordination compound, and this method is an effective means because in many cases the reaction speed is accelerated thereby. It is possible to control the size of the inorganic dispersion by adding water to the coordination product obtained thereby and performing hydrolysis.

An organic acid salt such as a formate, acetate, oxalate, and the like of a mineral acid such as nitric acid, sulfuric acid, carbolic acid, and hydrochloric acid, or an alkoxide and the like thereof is used as the starting material for the rare earth metal or/and Period IV transition metal. In consideration of reducing anionic impurities and the like, the use of an organic acid salt such as a formate, acetate, oxalate and the like and an alkoxide is preferred. The use of acetate is even more preferred. The acetate of a rare earth metal/and Period IV transition metal normally contains water of crystallization, and can be used unchanged depending on the type of metal to be coordinated, but before the reaction it is preferable to perform a dehydration treatment.

The functional group R of the dispersion phase shown in FIG. 1 is not particularly limited, and is selected depending on the type of organic polymer forming the composite. To increase the miscibility with the organic polymer, it is possible to make the selection with the purpose of imparting properties to make it polymerizable with the organic polymer or the monomer ingredients that can form the organic polymer. For example, R can be a hydrogen, alkyl group, reactive vinyl group, aryl group, diazo group, nitro group, cinnamoyl group, acryloyl group, imide group, epoxy group, cyano group, or an alkyl group, alkyl silyl group, alkyl carbonyl group and the like containing these functional groups.

In addition, provided it can form a uniform composite with the polymer forming the composite, an organic polymer having a functional group containing an active hydrogen such as a carboxylate group such as poly (meth) acrylic acid, polyethylene glycol, polyethylene oxide, cellulose and the like, a hydroxyl group, an amino group, an amide group, and the like can be used.

The following methods can be used for introducing the functional group R into the inorganic dispersion phase: (1) a method wherein insertion is performed by a reaction after the inorganic dispersion phase has been formed; and (2) a method wherein the R group is inserted beforehand into an alkoxide as the starting material that can coordinate with the rare earth metal or/and Period IV transition metal, and then a rare earth metal salt or/and Period IV transition metal salt is reacted thereto.

The compound to be reacted with the inorganic dispersion phase is not particularly limited provided it can form the aforementioned intended structure, and the following are preferably used: For method (1), a compound having a terminal active hydrogen such as a carboxylate group, hydroxyl group, amino group, amide group, and the like; and for method (2) a compound that can react with the inorganic dispersion phase by condensation such as an alkoxysilane containing an alkyl group, reactive vinyl group, aryl group, diazo group, nitro group cinnamoyl group, acryloyl group, imide group, epoxy group, cyano group, or an alkyl group containing these functional groups (R1R2R3SiOR4, wherein R1 is an alkyl group, reactive vinyl group, aryl group, diazo group, nitro group, cinnamoyl group, acryloyl group, imide group, epoxy group, cyano group, or an alkyl group containing these functional groups, R2 and R3 each represents a hydrogen atom, alkyl group, reactive vinyl group, aryl group, diazo group, nitro group, cinnamoyl group, acryloyl group, imide group, epoxy group, cyano group, or an alkyl or alkoxyl group containing these functional groups, and R4 is an alkyl group); an alkoxygermane (R1R2R3GeOR4, wherein R1 is an alkyl group, reactive vinyl group, aryl group, diazo group, nitro group, cinnamoyl group, acryloyl group, imide group, epoxy group, cyano group, or an alkyl group containing these functional groups, R2 and R3 each represents a hydrogen atom, alkyl group, reactive vinyl group, aryl group, diazo group, nitro group, cinnamoyl group, acryloyl group, imide group, epoxy group, cyano group, or an alkyl or alkoxyl group containing these functional groups, and R4 is an alkyl group) and the like.

[Organic Polymer] The organic polymer is not particularly limited provided dispersion is possible without aggregation of the rare earth metal/and Period IV transition metal wherein another metal is coordinated thereto, but preferably an organic polymer is used that has substantial transparency in the waveband region wherein the expression of optical function is to be utilized. The waveband region wherein the expression of optical function is to be utilized is not particularly limited to violet-red visible bands, and regions of UV light and x-rays with a wavelength shorter than the approximately 400 nm wavelength of violet, and infrared light with a wavelength longer than the approximately 750 nm wavelength of red light can also be used. The following can be listed as examples of the organic polymer, but the organic polymer of the present invention is by no means limited thereto: polymethyl methacrylate, polycyclohexyl methacrylate, polybenzyl methacrylate, polyphenyl methacrylate, polycarbonate, polyethylene terephthalate, polystyrene, polytetrafluoroethylene, poly-4-methylpentene-1, polyvinyl alcohol, polyethylene, polyacrylonitrile, styrene-acrylonitrile copolymer, polyvinyl chloride, polyvinyl carbazole, styrene-maleic anhydride copolymer, polyolefin, polyimide, epoxy resin, polysiloxane, polysilane, polyamide, cyclic olefin resin, and the like. The organic polymer can be used alone, or a combination of two or more organic polymers can be used.

The organic polymer can be worked into the form of the intended organic/inorganic composite containing a rare earth metal/and Period IV transition metal by dissolving the same in a solvent or by melting it by heating and the like, and it is possible to polymerize the organic polymer in the process of working it into the form of the intended organic/inorganic composite by using a mixture of an organic polymer precursor such as a monomer, an oligomer, or a monomer and oligomer, and the organic polymer.

In addition, these organic polymers may have functional groups that promote an addition, crosslinking, polymerization, or other type of reaction initiated by light and heat on the main chain or side chain thereof. Examples of such a functional group include a hydroxyl group, carbonyl group, carboxyl group, diazo group, nitro group, cinnamoyl group, acryloyl group, imide group, epoxy group, and the like.

The organic polymer may include an additive such as a stabilizer such as a plasticizer, antioxidant, and the like, a surfactant, a solubilization promoter, polymerization inhibitor, and a colorant such as a dye, pigment, and the like. In addition, the organic polymer may include a solvent (water, alcohol, glycol, Cellosolve, ketone, ester, ether, amide, or organic solvent such as a hydrocarbon and the like) to enhance molding properties such as coating performance and the like.

The present invention is described in greater detail below through examples, but the present invention is by no means limited to these examples.

EXAMPLE 1

<Preparation of Inorganic Dispersion Phase> Erbium acetate that had been dehydrated for 1 hour at 110° C. and tri-s-butoxy aluminum were added together in 2-butanol (Er/Al=3 molar, mathematically converted concentration of total oxides of Er and Al 5 mass %) and refluxed for 1 hour to obtain a light pink transparent liquid. The particle size of the reaction product obtained thereby was measured using dynamic light scattering, and it was confirmed that the reaction product comprised composite nanoparticles with a peak top of 1.7 nm in diameter. In addition, coordination of the Al via an oxygen atom(s) with the Er was verified before and after the reaction with tri-s-butoxy aluminum by the change in 27Al-NMR spectrum.

<Preparation of Composite of Inorganic Dispersion Phase and Transparent Organic Polymer>

A photopolymerizable acrylic resin "Cyclomer" (Daicel Chemical Industries, Ltd.) was used as the transparent organic polymer. This organic polymer, the composite nanoparticles containing ErAl prepared according to the above method, and a photoradical initiator "Irgacure 369" (Ciba Specialty Chemicals) were mixed together in PGMEA, and stirred for 2 hours at room temperature to obtain a liquid mixture. The mixture ratio was controlled so that the Er contents are 5.2% and 0.52% in mass in terms of solid content of the composite.

After bonding a frame of polytetrafluoroethylene plates to a fused quartz plate as a mold, the liquid mixture formulated as noted above was poured into the interior of the polytetrafluoroethylene mold, and an approximately 1 mm thick cast molded product of the organic/inorganic composite containing a rare earth metal was obtained by evaporating the PGMEA at 100° C. and drying. The transmittance value of the molded product obtained thereby was 93% at a wavelength of 633 nm, which was equivalent to the transmittance value of the organic polymer not doped by the rare earth metal, and it was confirmed that optical transparency can be assured.

<Measurement of Photoluminescence Intensity>

Figure 2:
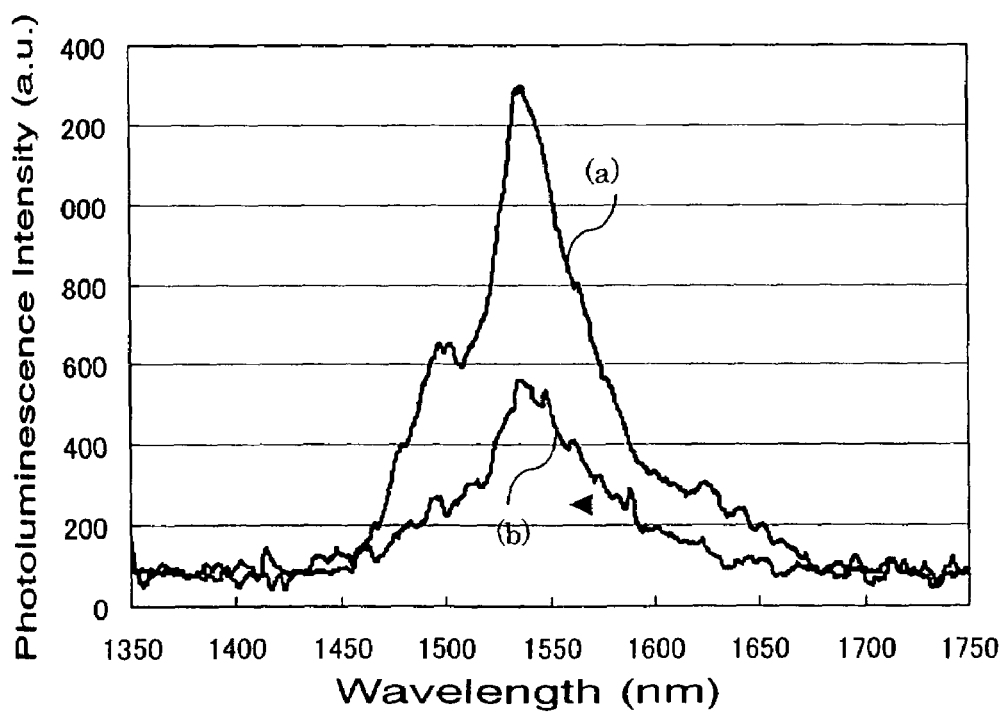
FIG. 2 is a diagram showing the photoluminescence spectrum of the organic/inorganic composite containing erbium used in Example 1 among the inorganic/organic composites of the present invention.

The organic/inorganic composite containing Er obtained in the above manner was irradiated with an argon laser at a wavelength of 514 nm, and the Photoluminescence intensity was measured. FIG. 2 is a graph of the fluorescence spectrum of the wavelengths of the composite nanoparticles containing Er—Al/photopolymerizable acrylic resin composite prepared in the above manner. In the drawing, (a) represents the fluorescence spectrum of a test sample containing an erbium (Er) concentration of 5.2%, and likewise (b) represents the fluorescence spectrum of a test sample containing a erbium concentration of 0.52%. As a result, as shown in FIG. 2, the fluorescence specific to erbium was observed in the vicinity of a wavelength of 1550 nm. Based on these results, it was confirmed that even when doped with a high concentration of the rare earth metal, quenching is controlled and the emission process of Er can be expressed thereby.

EXAMPLE 2

Preparation of the Inorganic Dispersion Phase

Neodymium acetate that had been dehydrated under vacuum for 1 hour at 110° C. and tri-s-butoxy aluminum were added together in propylene glycol α-monomethyl ether (Nd/Al=3 molar, mathematically converted concentration of total oxides of Er and Al 5 mass %) and refluxed for 1 hour to obtain a light purple transparent liquid. The particle size of the reaction product obtained thereby was measured using dynamic light scattering, and it was confirmed that the reaction product comprised composite nanoparticles with a peak top of 2.3 nm in diameter. In addition, coordination of the Al via an oxygen atom(s) with the Nd was verified before and after the reaction with tri-s-butoxy aluminum by the change in 27Al-NMR spectrum.

<Preparation of Composite of Inorganic Dispersion Phase and Transparent Organic Polymer>

Hydroxypropyl cellulose (Nippon Soda Co., Ltd.) was used as the transparent organic polymer. This organic polymer and the composite nanoparticles containing NdAl prepared according to the above method were mixed together in Ethyl Cellosolve, and stirred for 2 hours at room temperature to obtain a liquid mixture. The mixture ratio was controlled so that the neodymium (Nd) content is 8% in mass in terms of solid content of the composite.

The liquid mixture formulated as noted above was poured into a polytetrafluoroethylene container used as mold, and an approximately 1 mm thick cast molded product of the organic/inorganic composite containing Nd was obtained by evaporating the Ethyl Cellosolve at 120° C. and drying.

<Measurement of Spectroscopic Absorption Properties>

Figure 3:
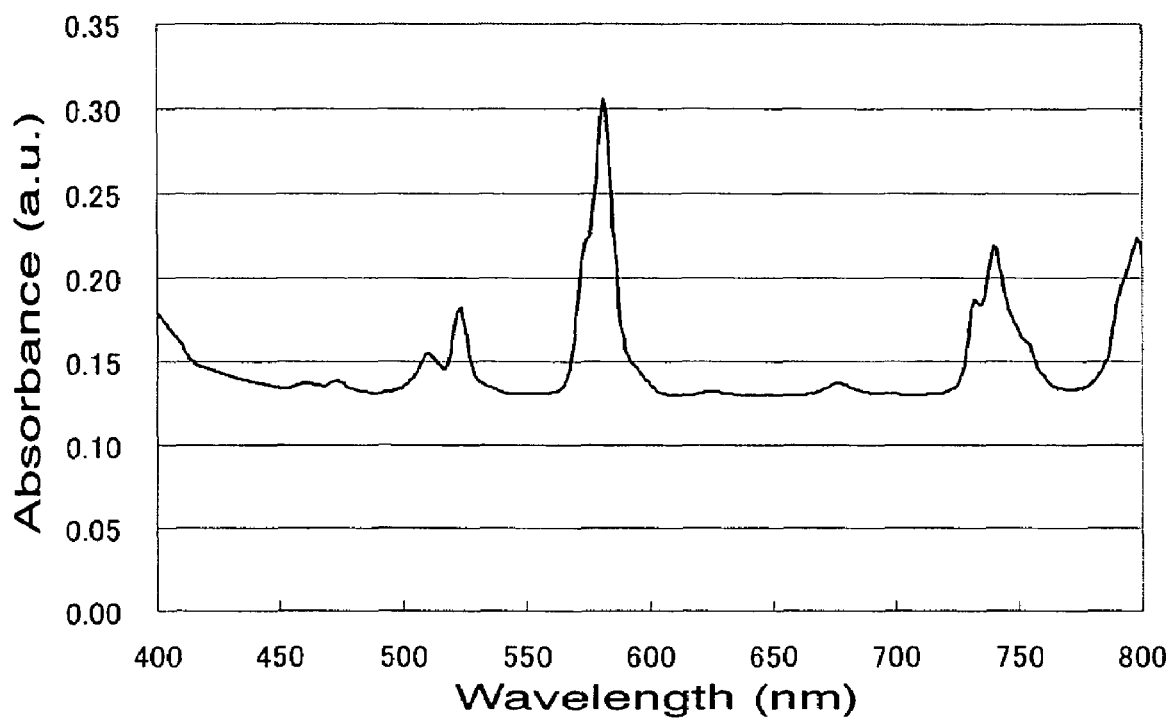
FIG. 3 is a spectrogram showing the absorption spectrum of the organic/inorganic composite containing neodymium used in Example 2 among the organic/inorganic composites containing a rare earth metal or/and Period IV transition metal of the present invention.

The spectroscopic absorption properties of the organic/inorganic composite containing Nd obtained thereby was measured using a spectrophotometer. FIG. 3 shows the spectroscopic absorption spectrum of the composite nanoparticles containing Nd—Al/hydroxypropyl cellulose composite prepared according to the above method. It is clear that absorption in the wavebands of approximately 500 to 540 nm and approximately 560 to 600 nm originating from the Nd absorption can be assured in the composite nanoparticles containing Nd—Al/hydroxypropyl cellulose composite.

Figure 4:
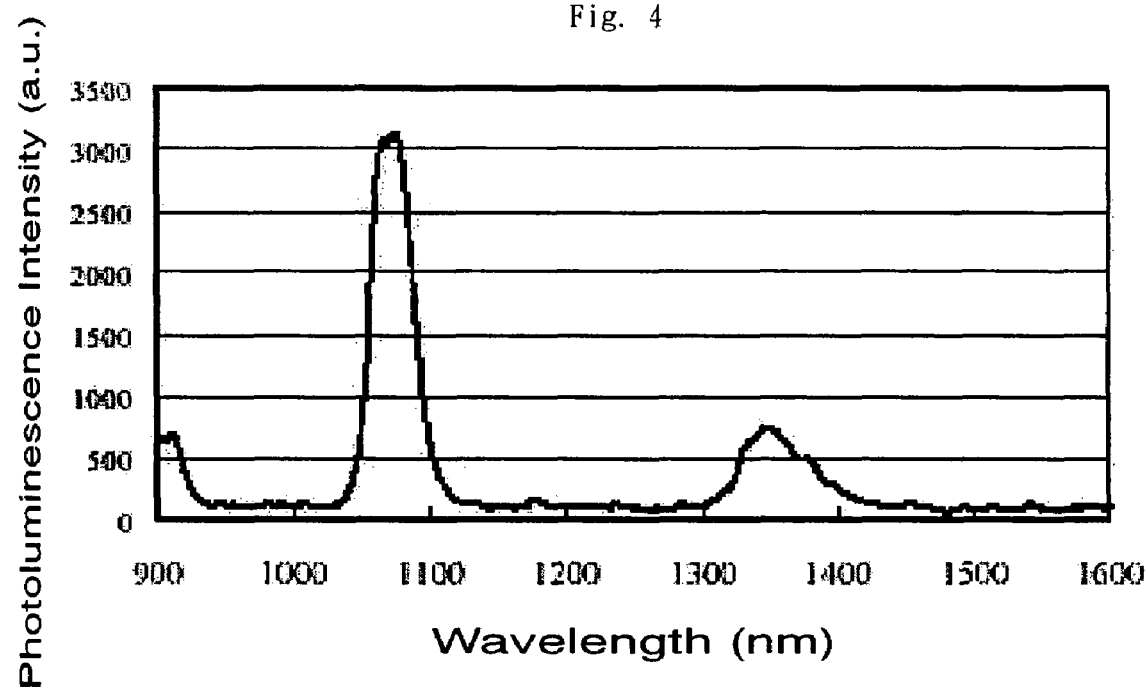
FIG. 4 is a graph showing the photoluminescence spectrum of the wavelength specific to the composite nanoparticles containing NdAl/photopolymerized acrylic resin composite prepared according to the above method.

<Measurement of Photoluminescence Intensity> The organic/inorganic composite containing Nd obtained in the above manner was irradiated with an argon laser at a wavelength of 514 nm, and the Photoluminescence intensity was measured. FIG. 4 is a graph of the fluorescence spectrum of the wavelengths of the composite nanoparticles containing Nd—Al/photopolymerizable acrylic resin composite prepared in the above manner. As a result, as shown in FIG. 4, the fluorescence specific to neodymium (Nd) was observed in the vicinity of a wavelength of 1075 nm. Based on these results, it was confirmed that even when doped with a high concentration of the rare earth metal, quenching is suppressed and the emission process of neodymium can be expressed thereby.

EXAMPLE 3

Preparation of the Inorganic Dispersion Phase

Neodymium acetate that had been dehydrated under vacuum for 1 hour at 110° C. and tri-s-butoxy aluminum were added together in propylene glycol α-monomethyl ether (Eu/Al=3 molar, mathematically converted concentration of total oxides of Eu and Al 5 mass %) and refluxed for 1 hour to obtain a colorless transparent liquid. The particle size of the reaction product obtained thereby was measured using dynamic light scattering, and it was confirmed that the reaction product comprised composite nanoparticles with a peak top of 1.5 nm in diameter. In addition, coordination of the Al via an oxygen atom(s) with the Eu was verified before and after the reaction with tri-s-butoxy aluminum by the change in 27Al-NMR spectrum.

<Preparation of Composite of Inorganic Dispersion Phase and Transparent Organic Polymer>

Hydroxypropyl cellulose (Nippon Soda Co., Ltd.) was used as the transparent organic polymer. This organic polymer and the composite nanoparticles containing Eu—Al prepared according to the above method were mixed together in Ethyl Cellosolve, and stirred for 2 hours at room temperature to obtain a liquid mixture. The mixture ration was controlled so that the europium (Eu) content is 8% in mass in terms of solid content of the composite.

The liquid mixture formulated as noted above was poured into a polytetrafluoroethylene container used as mold, and an approximately 1 mm thick cast molded product of the organic/inorganic composite containing Eu was obtained by evaporating the Ethyl Cellosolve at 120° C. and drying.

Figure 5:
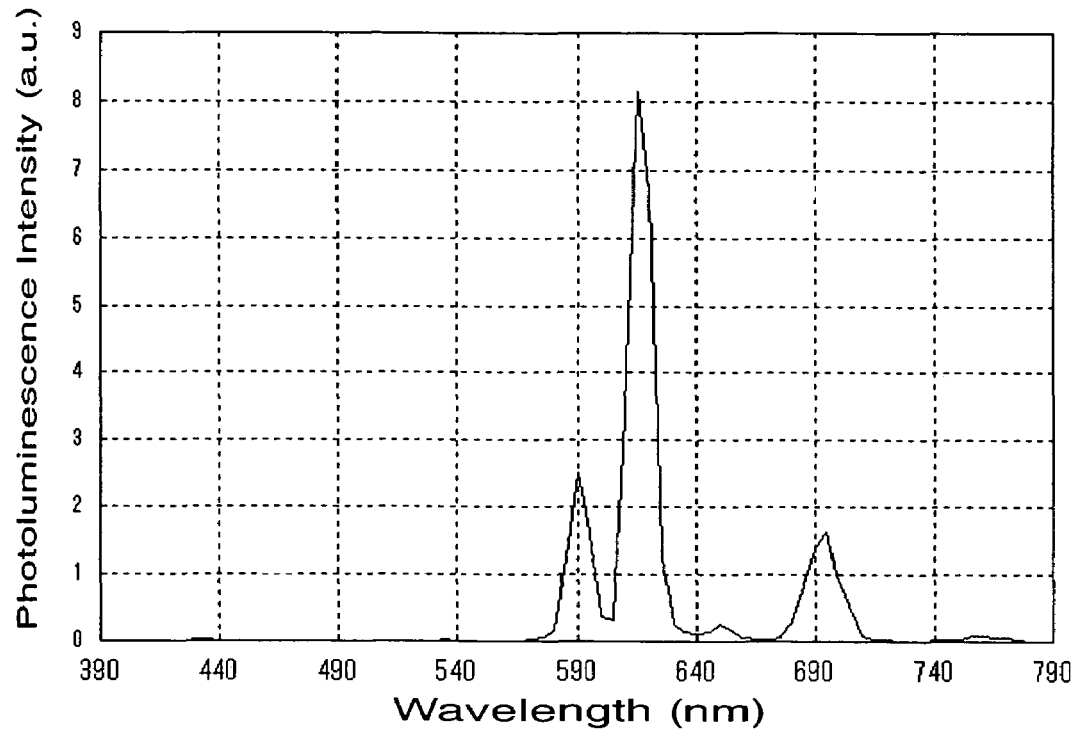
FIG. 5 is a graph showing the photoluminescence spectrum of the wavelength specific to the composite nanoparticles containing EuAl/photopolymerized acrylic resin composite.

<Measurement of Photoluminescence Intensity> The organic/inorganic composite containing Eu obtained in the above manner was irradiated with a xenon laser at a wavelength of 380 nm extracted by a filter, and the Photoluminescence intensity was measured. FIG. 5 is a graph of the fluorescence spectrum of the wavelengths of the composite nanoparticles containing EuAl/photopolymerizable acrylic resin composite prepared in the above manner. As a result, as shown in FIG. 5, the fluorescence specific to europium was observed in the vicinity of a wavelength of 615 nm.

EXAMPLE 4

<Preparation of Composite of Inorganic Dispersion Phase>and Transparent Organic Polymer An amount of methacrylic acid equivalent to double the molar amount of Al was added to the composite nanoparticles containing Eu—Al prepared in Example 3, and after the mixture was stirred for 2 hours at room temperature, the solvent was removed under vacuum at 40° C. or lower to obtain a colorless transparent syrup-like residue. After methyl methacrylate was added to the colorless transparent residue to reconstitute a transparent liquid, pentaerythritol tetraacrylate and Irgacure 149 were added (methyl methacrylate/pentaerythritol tetraacetate:mass ratio 90/10, Irgacure 149=1.5% with respect to acrylic monomer), and a solid, transparent organic/inorganic composite containing 5 mass % Eu was obtained by irradiating the mixture in a 5 mm diameter glass container with a high pressure mercury vapor lamp. The red luminescence characteristic of Eu was observed by irradiating the organic/inorganic containing Eu obtained thereby with a UV-emitting LED at a wavelength of 395 nm.

EXAMPLE 5

<Preparation of Inorganic Dispersion Phase>

Terbium acetate that had been dehydrated under vacuum for 1 hour at 110° C. and tri-s-butoxy aluminum were added together in propylene glycol α-monomethyl ether (Tb/Al=3 molar, mathematically converted concentration of total oxides of Tb and Al 5 mass %) and refluxed for 1 hour to obtain a colorless transparent liquid. The particle size of the reaction product obtained thereby was measured using dynamic light scattering, and it was confirmed that the reaction product comprised composite nanoparticles with a peak top of 2.3 nm in diameter. In addition, coordination of the Al via an oxygen atom(s) with the Tb was verified before and after the reaction with tri-s-butoxy aluminum by the change in 27Al-NMR spectrum.

<Preparation of Composite of Inorganic Dispersion Phase and Transparent Organic Polymer>

Hydroxypropyl cellulose (Nippon Soda Co., Ltd.) was used as the transparent organic polymer. This organic polymer and the composite nanoparticles containing Tb—Al prepared according to the above method were mixed together in Ethyl Cellosolve, and stirred for 2 hours at room temperature to obtain a liquid mixture. The mixture ratio was controlled so that the Tb content is 8% in mass in terms of solid content of the composite.

The liquid mixture formulated as noted above was poured into a polytetrafluoroethylene container used as mold, and an approximately 1 mm thick cast molded product of the organic/inorganic composite containing Tb was obtained by evaporating the Ethyl Cellosolve at 120° C. and drying.

Figure 6:
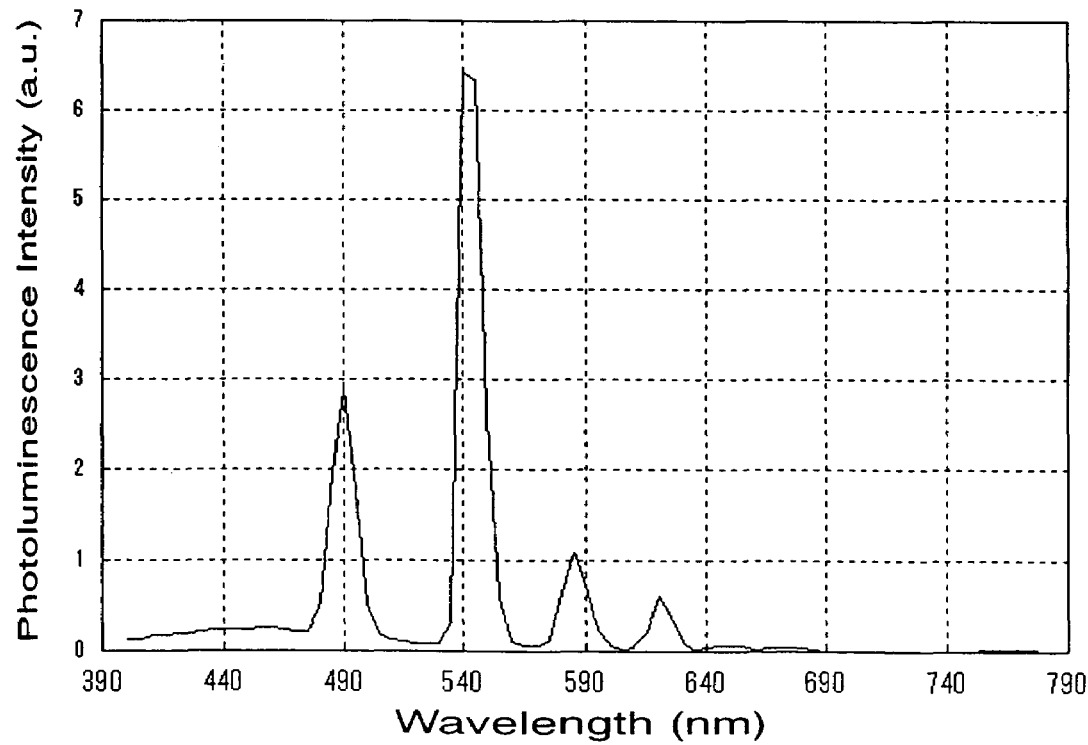
FIG. 6 is a graph showing the photoluminescence spectrum of the wavelength specific to the composite nanoparticles containing TbAl/photopolymerized acrylic resin composite prepared according to the above method.

<Measurement of Photoluminescence Intensity> The organic/inorganic composite containing Tb obtained in the above manner was irradiated with a xenon laser at a wavelength of 380 nm extracted by a filter, and the Photoluminescence intensity was measured. FIG. 6 is a graph of the fluorescence spectrum of the wavelengths of the composite nanoparticles containing Tb—Al/photopolymerizable acrylic resin composite prepared in the above manner. As a result, as shown in FIG. 6, the fluorescence specific to terbium (Tb) was observed in the vicinity of a wavelength of 540 nm.

EXAMPLE 6

<Preparation of the Inorganic Dispersion Phase>

Terbium acetate that had been dehydrated under vacuum for 1 hour at 110° C. and tetraisopropyl titanium were added together in propylene glycol α-monomethyl ether (Tb/Ti=3 molar, mathematically converted concentration of total oxides of Tb and Ti=5 mass %) and refluxed for 1 hour to obtain a colorless transparent liquid. The particle size of the reaction product obtained thereby was measured using dynamic light scattering, and it was confirmed that the reaction product comprised composite nanoparticles with a peak top of 1.0 nm in diameter.

<Preparation of Composite of Inorganic Dispersion Phase and Transparent Organic Polymer>

Hydroxypropyl cellulose (Nippon Soda Co., Ltd.) was used as the transparent organic polymer. This organic polymer and the composite nanoparticles containing TbTi prepared according to the above method were mixed together in Ethyl Cellosolve, and stirred for 2 hours at room temperature to obtain a liquid mixture. The mixture ratio was controlled so that the Tb content is 8% in mass in terms of solid content of the composite.

The liquid mixture formulated as noted above was poured into a polytetrafluoroethylene container used as mold, and an approximately 1 mm thick cast molded product of the organic/inorganic composite containing Tb was obtained by evaporating the Ethyl Cellosolve at 120° C. and drying.

Figure 7:
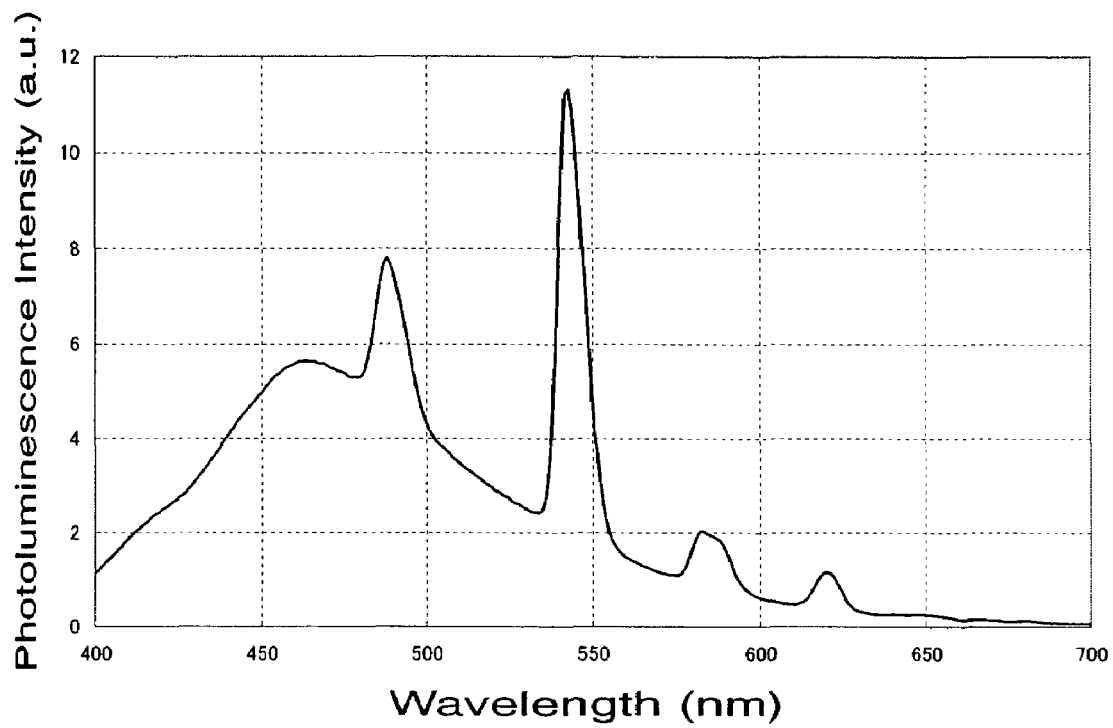
FIG. 7 is a graph showing the photoluminescence spectrum of the wavelength specific to the composite nanoparticles containing TbTi/photopolymerized acrylic resin composite prepared according to the above method.

<Measurement of Photoluminescence Intensity> The organic/inorganic composite containing Tb obtained in the above manner was irradiated with a xenon laser at a wavelength of 380 nm extracted by a filter, and the Photoluminescence intensity was measured. FIG. 7 is a graph of the fluorescence spectrum of the wavelengths of the composite nanoparticles containing Tb—Ti/photopolymerizable acrylic resin composite prepared in the above manner. As a result, as shown in FIG. 7, a broad emission with a peak wavelength near 465 nm was observed in addition to the fluorescence specific to terbium (Tb) that was observed in the vicinity of a wavelength of 540 nm. As a result, when we compare the results obtained in Example 5 and those in Example 6, it is clear that emission properties can be controlled by changing the metal coordinating with Tb via an oxygen atom(s) from Al to Ti.

EXAMPLE 7

<Preparation of Composite of Inorganic Dispersion Phase and Transparent Organic Polymer>

An amount of methacrylic acid equivalent to double the molar amount of Al was added to the composite nanoparticles containing Tb—Al prepared in Example 5, and after the mixture was stirred for 2 hours at room temperature, the solvent was removed under vacuum at 40° C. or lower to obtain a colorless transparent syrup-like residue. After methyl methacrylate was added to the colorless transparent residue to reconstitute a transparent liquid, pentaerythritol tetraacrylate and Irgacure 149 were added (methyl methacrylate/pentaerythritol tetraacetate:mass ratio 90/10, Irgacure 149=1.5% with respect to acrylic monomer), and a solid, transparent organic/inorganic composite containing 5 mass % Tb was obtained by irradiating the mixture in a 5 mm diameter glass container with a high pressure mercury vapor lamp. The green luminescence characteristic of Tb was observed by irradiating the organic/inorganic containing Tb obtained thereby with a UV-emitting LED at a wavelength of 395 nm.

EXAMPLE 8

<Preparation of the Inorganic Dispersion Phase>

Cerium acetate that had been dehydrated under vacuum for 1 hour at 110° C. was added to propylene glycol α-monomethyl ether and heat-treated at 100° C. for 24 hours. Then tri-s-butoxy aluminum was added (Ce/Al=3 molar, mathematically converted concentration of total oxides of Ce and Al 5 mass %) and the mixture was refluxed for 1 hour to obtain a pale yellow transparent liquid.

<Preparation of Composite of Inorganic Dispersion Phase and Transparent Organic Polymer>

Hydroxypropyl cellulose (Nippon Soda Co., Ltd.) was used as the transparent organic polymer. This organic polymer and the composite nanoparticles containing Ce—Al prepared according to the above method were mixed together in Ethyl Cellosolve, and stirred for 2 hours at room temperature to obtain a liquid mixture. The mixture ratio was controlled so that the Ce content is 8% in mass in terms of solid content of the composite.

The liquid mixture formulated as noted above was poured into a polytetrafluoroethylene container used as mold, and an approximately 1 mm thick cast molded product of the organic/inorganic composite containing Ce was obtained by evaporating the Ethyl Cellosolve at 120° C. and drying.

<Measurement of Photoluminescence Intensity>

Figure 8:
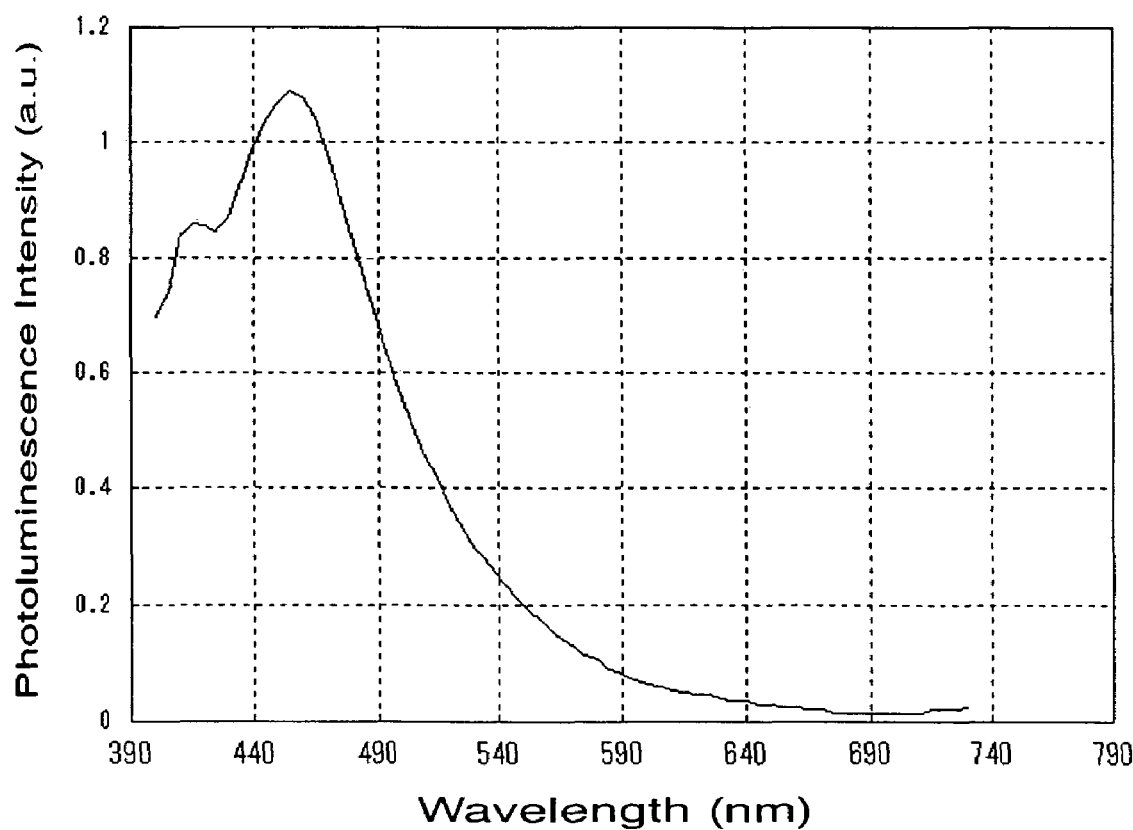
FIG. 8 is a graph showing the photoluminescence spectrum of the wavelength specific to the composite nanoparticles containing CeAl/photopolymerized acrylic resin composite.

The organic/inorganic composite containing Ce obtained in the above manner was irradiated with a xenon laser at a wavelength of 380 nm extracted by a filter, and the Photoluminescence intensity was measured. FIG. 7 is a graph of the fluorescence spectrum of the wavelengths of the composite nanoparticles containing Ce—Al/photopolymerizable acrylic resin composite prepared in the above manner. As a result, as shown in FIG. 8, the fluorescence specific to cerium (Ce) that was observed in the vicinity of a wavelength range of 400 to 500 nm.

EXAMPLE 9

<Preparation of Composite of Inorganic Dispersion Phase>and Transparent Organic Polymer An amount of methacrylic acid equivalent to double the molar amount of Al was added to the composite nanoparticles containing Ce—Al prepared in Example 8, and after the mixture was stirred for 2 hours at room temperature, the solvent was removed under vacuum at 40° C. or lower to obtain a colorless transparent syrup-like residue. After methyl methacrylate was added to the colorless transparent residue to reconstitute a transparent liquid, pentaerythritol tetraacrylate and Irgacure 149 were added (methyl methacrylate/pentaerythritol tetraacetate:mass ratio 90/10, Irgacure 149=1.5% with respect to acrylic monomer), and a solid, transparent organic/inorganic composite containing 5 mass % Ce was obtained by irradiating the mixture in a 5 mm diameter glass container with a high pressure mercury vapor lamp. The blue luminescence characteristic of Ce was observed by irradiating the organic/inorganic containing Tb obtained thereby with a UV-emitting LED at a wavelength of 395 nm.

EXAMPLE 10

<Preparation of the Inorganic Dispersion Phase>

Praseodymium acetate that had been dehydrated for 1 hour at 110° C. and tri-s-butoxy aluminum were added together in propylene glycol-α-monomethyl ether (Pr/Al=3 molar, mathematically converted concentration of total oxides of Pr and Al 5 mass %) and refluxed for 1 hour to obtain a light green transparent liquid. The particle size of the reaction product obtained thereby was measured using dynamic light scattering, and it was confirmed that the reaction product comprised composite nanoparticles with a peak top of 6.5 nm in diameter. In addition, coordination of the Al via an oxygen atom(s) with the Pr was verified before and after the reaction with tri-s-butoxy aluminum by the change in 27Al-NMR spectrum.

<Preparation of Composite of Inorganic Dispersion Phase and Transparent Organic Polymer>

A photopolymerizable acrylic resin "Cyclomer" (Daicel Chemical Industries, Ltd.) was used as the transparent organic polymer. This organic polymer, the composite nanoparticles containing PrAl prepared according to the above method, and a photoradical initiator "Irgacure 369" (Ciba Specialty Chemicals) were mixed together in PGMEA, and stirred for 2 hours at room temperature to obtain a liquid mixture. The mixture ratio was controlled so that the praseodymium (Pr) content is 10% in mass in terms of solid content of the composite.

Using a polytetrafluoroethylene container as a mold, an approximately 1 mm thick transparent cast molded product of the organic/inorganic composite containing Pr was obtained by evaporating the PGMEA at 120° C. and drying.

<Measurement of Spectroscopic Absorption Properties>

Figure 9:
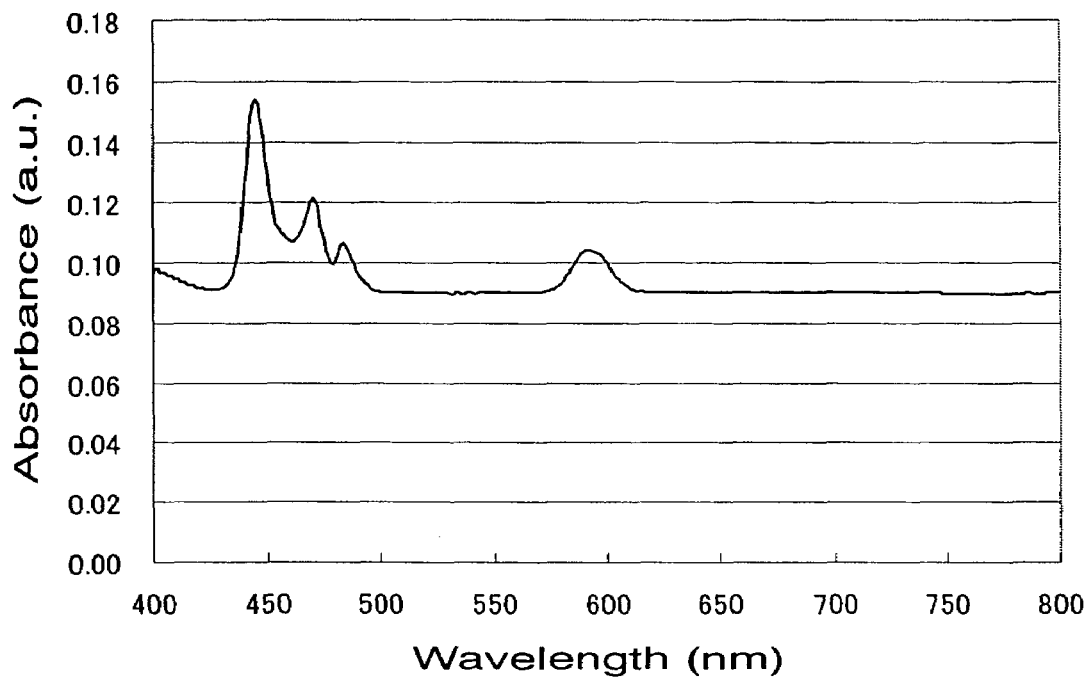
FIG. 9 is an absorption spectrogram of the organic/inorganic composite containing Pr—Al used in Example 10 among the organic/inorganic composites of the present invention.

The spectroscopic absorption properties of the organic/inorganic composite containing Pr obtained thereby was measured using a spectrophotometer. FIG. 9 shows the spectroscopic absorption spectrum of the composite nanoparticles containing PrAl/photopolymerizable acrylic resin composite prepared according to the above method. It is clear that absorption in the wavebands of approximately 440 to 490 nm originating from the Pr absorption can be assured in the composite nanoparticles containing Ni—Nb/photopolymerizable acrylic resin composite.

EXAMPLE 11

<Preparation of the Inorganic Dispersion Phase>

Nickel acetate that had been dehydrated for 1 hour under vacuum at 100° C. and pentaethoxy niobium were added together in ethylene glycol monomethyl ether (Ni/Nb=2 molar, mathematically converted concentration of total oxides of Ni and Nb 5 mass %) and refluxed for 1 hour to obtain a green transparent liquid. The particle size of the reaction product obtained thereby was measured using dynamic light scattering, and it was confirmed that the reaction product comprised composite nanoparticles with a peak top of 2.9 nm in diameter.

<Preparation of Composite of Inorganic Dispersion Phase and Transparent Organic Polymer>

Hydroxypropyl cellulose (Nippon Soda Co., Ltd.) was used as the transparent organic polymer. This organic polymer and the composite nanoparticles containing Ni—Nb prepared according to the above method were mixed together in Ethyl Cellosolve, and stirred for 2 hours at room temperature to obtain a liquid mixture. The mixture ratio was controlled so that the Ni content is 8% in mass in terms of solid content of the composite.

The liquid mixture formulated as noted above was poured into a polytetrafluoroethylene container used as mold, and an approximately 1 mm thick transparent cast molded product of the organic/inorganic composite containing Ni was obtained by evaporating the Ethyl Cellosolve at 120° C. and drying.

<Measurement of Spectroscopic Transmittance Value>

Figure 10:
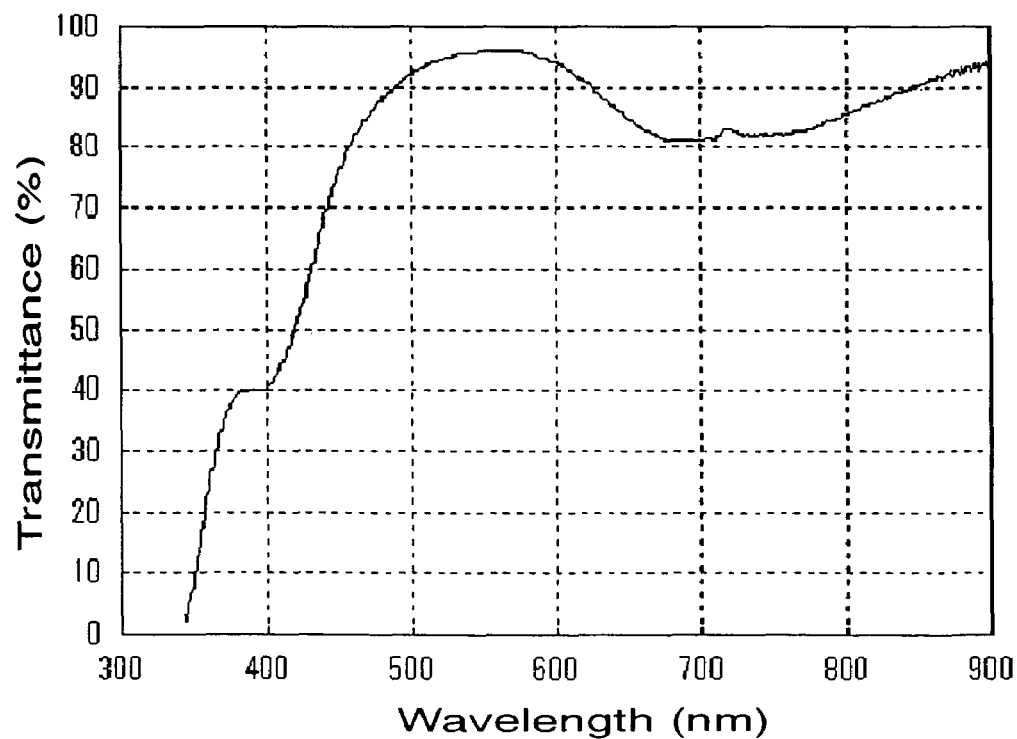
FIG. 10 is an absorption spectrum of the organic/inorganic composite containing Ni used in Example 11 among the organic/inorganic composites of the present invention.

The spectroscopic absorption properties of the organic/inorganic composite containing Ni obtained thereby was measured using a spectrophotometer. FIG. 10 shows the spectroscopic absorption spectrum of the composite nanoparticles containing the Ni—Nb/hydroxypropyl cellulose composite prepared according to the above method. It is clear that absorption in the wavebands of approximately 900 to 600 nm and approximately 450 nm or less originating from the Ni absorption can be assured in the composite nanoparticles containing Ni—Nb/hydroxypropyl cellulose composite.

Based on the above results the present invention makes it possible to provide an organic/inorganic composite wherein a rare earth metal or/and Period IV transition metal is doped at a high concentration in an organic polymer, and the original absorption properties of the doping elements can be expressed thereby. In addition, by doping with a rare earth metal it can be assured that quenching, which has been impossible to avoid with conventional, high concentration doping can be controlled and that the luminescent process specific to each doping element can be expressed.

COMPARISON EXAMPLE

The solubility in organic solvents and dispersion properties in organic polymers of the metal salts and oxides of various rare earth or/and Period IV transition metals were demonstrated, but it was not possible to obtain transparent solutions and transparent dispersions.

The present invention relates to an organic/inorganic composite that is a composite of a rare earth metal or/and a period IV transition metal and an organic polymer to be used most suitably in fields involving optical function applications wherein the transmission, refraction, reflection, polarization plane rotation, and the like of incident light are controlled, and functions such as luminescence (fluorescence) due to excitation by incident light, amplification, and the like are expressed. Various optical functions can be expressed by selecting the rare earth metal or/and Period IV transition metal salt, type of coordinating metal or organic polymer in accordance with the purpose and by forming the organic/inorganic composite containing a rare earth metal or/and Period IV transition metal in accordance with the intended use. A high index material can be listed as such an example. In the past cerium, lanthanum, and the like have been used to make a glass lens highly refractive. The present invention can be utilized to make an organic polymer material highly refractive because the rare earth metal therein can be dispersed in the organic polymer at a high concentration. Materials for parts having a magneto-optical effect such as magneto-optical recording disks and the like can be listed as an application of the present invention. In the past, gadolinium, terbium, and the like have been used for this application, but the disks have been formed by vacuum deposition, sputtering, and the like. The present invention can be applied to applied to a wide range of plastic bodies from thin films to bulk compacts using inexpensive means such as coating, casting, and the like because these rare earth metals can be dispersed within an organic polymer. Light control optical materials can also be listed as an application of the present invention. In the past colored glass materials have been obtained wherein color rending is controlled by doping glass with a rare earth metal such as cerium, praseodymium, erbium, neodymium, and the like, and such materials have been used in electric lamps that enhance the coloring of food on a table, sunglasses, and the like. The present invention can be used to prepare optical resins wherein the color rendering is adjusted by doping an organic polymer with the rare earth metals in accordance with the present invention. An optical amplifier can also be listed as an application of the present invention. In the past erbium, thulium, praseodymium, dysprosium, and the like have been doped into optical fiber and used as an optical fiber amplifier. The present invention can be applied to the preparation of a plastic optical fiber type amplifier and a thin film optical waveguide type amplifier by dispersing the rare earth metals therein in an organic polymer. More specifically, in the past even with glass that was easier than an organic polymer to dope with a rare earth metal, because quenching occurs more easily as the doping concentration increases, optical amplifiers with a doping concentration of 100 ppm were realized by making them longer, but there was a problem because they could not be made more compact; however, the organic/inorganic composite containing a rare earth metal obtained by the present invention can be applied to the manufacture of a compact optical amplifier. In addition to the above industrial applications, the present invention can be applied to biosensors, color displays, light emitting elements and the like that utilize the light emission properties of the rare earth metal/Period IV transition metal therein. In addition, by making use of the desirable feature of easy processability generally provide by an organic polymer, it becomes possible to apply objects of various shapes such as a thin film, sheet, fiber, compact, and the like to the aforementioned functions.

Figure 11:
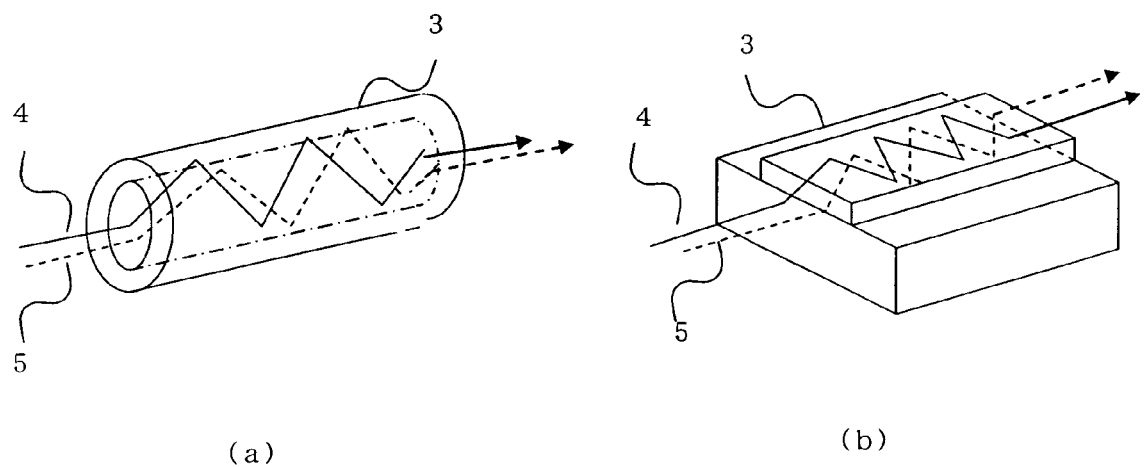
FIG. 11($a$) is a schematic diagram showing the basic structure of an optical amplifier that is an optical fiber amplifier.

Objects having structures such as those shown in FIGS. 11(a) and (b) can be used as an optical waveguide in the optical amplifier of the present invention. Normally, FIG. 11(a) will be called a fiber type, and FIG. 11(b) will be called an optical waveguide type. In both cases, light is propagated while enclosed in a relatively highly refractive member (core).

In the optical amplifier 3 the signal light 4 is propagated, and simultaneously the excitation light 5 is also propagated. Normally, an optical coupler is attached in front of and behind the optical amplifier, and light is amplified by placing the excitation light on the optical waveguide wherein the signal light 4 is propagated, or behind the optical amplifier the excitation light 5 is isolated from that transmission waveguide.

The optical waveguide of the present invention is formed by the organic/inorganic composite containing a rare earth metal.

EXAMPLE 12

<Preparation of Inorganic Dispersion Phase>

Erbium acetate that had been dehydrated for 1 hour at 110° C. and tri-s-butoxy aluminum were added together in 2-butanol (Er/Al=3 molar, mathematically converted concentration of total oxides of Er and Al 5 mass %) and refluxed for 1 hour to obtain a light pink transparent liquid. The particle size of the reaction product obtained thereby was measured using dynamic light scattering, and it was confirmed that the reaction product comprised composite nanoparticles with a peak top of 1.7 nm in diameter. In addition, coordination of the Al via an oxygen atom(s) with the Er was verified before and after the reaction with tri-s-butoxy aluminum by the change in 27Al-NMR spectrum.

<Preparation of Composite of Inorganic Dispersion Phase and Transparent Organic Polymer>

A photopolymerizable acrylic resin "Cyclomer" (Daicel Chemical Industries, Ltd.) was used as the transparent organic polymer. This organic polymer, the composite nanoparticles containing Er—Al prepared according to the above method, and a photoradical initiator "Irgacure 369" (Ciba Specialty Chemicals) were mixed together in propylene glycol monomethyl ether acetate (PGMEA), and stirred for 2 hours at room temperature to obtain a liquid mixture. The mixture ratio was controlled so that the erbium contents are 5.2% and 0.52% in mass in terms of solid content of the composite.

After a liquid mixture prepared in the above manner was rotary coated on a fused quartz plate using a spinner, the residual solvent was removed by drying for 1 minute on a plate heater at 90° C. to obtain a thin film of organic/inorganic composite containing Er—Al and having an optical polymer acrylic resin as a matrix material. In addition, the thin film was exposed to light using an ultrahigh pressure mercury lamp via a photomask wherein a 7 μm wide straight line waveguide pattern was drawn. Next the parts that were not exposed to the ultrahigh pressure mercury lamp were dissolved and removed by immersing the plate for 10 seconds in alkali water (2.3% aqueous solution of TMAH). Finally, after drying for 2 minutes at 90° C., a 7 μm wide, 2.8 μm thick organic/inorganic composite waveguide comprising an optical polymeric acrylic resin and an Er—Al inorganic dispersion phase was obtained on the quartz plate.

<Measurement of Optical Amplifying Properties>

Figure 12:
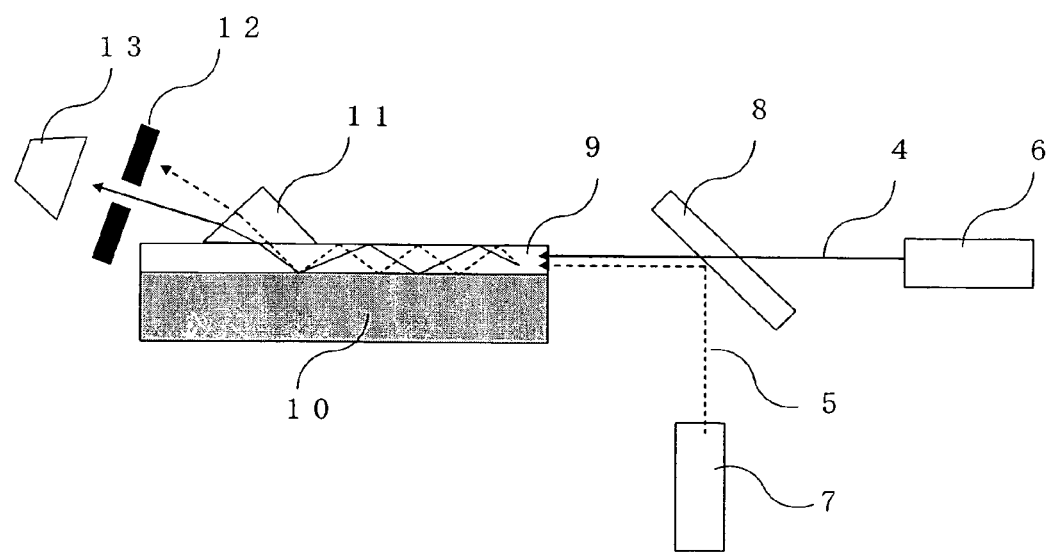
FIG. 12 is an optics diagram measuring the optical amplification properties using an optical waveguide amplifier comprising the Er—Al organic/inorganic composite prepared in Example 12 among the optical amplifiers of the present invention.

The optical amplifying properties of the organic/inorganic composite waveguide comprising an optical polymeric acrylic resin and an Er—Al inorganic dispersion phase obtained thereby were measured using an optics system such as that shown in FIG. 12. A 1550 nm wavelength, 3 mW capacity semiconductor laser 6 was used as the light source for the signal light 4, and a 983 nm wavelength, 150 mW peak capacity semiconductor pulse laser 7 was used as the light source for the excitation light 5. The excitation light 5 was superimposed onto the optical axis of the signal light 4 using a dichroic mirror 8 having high reflectivity only near a wavelength of 980 nm, and joined at the end of the organic/inorganic composite waveguide 9 comprising a rare earth metal wherein both lights were formed. In addition, to extract only the signal light 4 and measure the intensity, after both lights were propagated in the waveguide, the excitation light 5 was isolated with a prism 11 comprising SF6 glass by utilizing the principle that the angle of the outgoing beam differs according to the wavelength. Only the signal light 4 that had passed through a pin hole 12 was received by a photodetector 13 and the light intensity was measured using an oscilloscope.

As a result, it was confirmed that when the semiconductor pulse laser for excitation light was lit, the signal intensity was amplified with a gain equivalent to 3.8 dB in comparison to when it was not lit, thus verifying the function of the present invention as an optical amplifier.

The present invention can be suitably used with respect to an optical amplifier that amplifies the signal light intensity based on an excitation light. EDFA wherein a quartz based inorganic material is commercially used as a matrix material can be listed as an example of such an optical amplifier, and in accordance with the present invention the quartz based inorganic material can be replaced with an organic polymer, enabling the cost to be reduced thereby. In addition, because rare earth metals, which could only be doped at a concentration of about 50 to 100 ppm in the past, can now be doped at a concentration of 10% (100000 ppm) or more, the present invention enables the miniaturization of optical amplifiers that could only be realized on a long scale in the past. As a result, the optical amplifier of the present invention can display its effect not only in long distance, main line fiber optic nets that have been used in the past, but also in applications such as subscriber optical communications nets and the like wherein the number of downstream branches in the transmission waveguide increase and loss of optical transmission due to branching becomes a problem.

In addition, in the future the optical amplifier of the present invention can be displayed in the field of optical interconnections wherein research is advancing to break the bottleneck in information processing capacity and speed by using light rather than presently used electrons for transmission between and within circuit boards in computers.

The light control optical element of the present invention is a collective term for optical elements having important functions of controlling the transmission, refraction, focusing, scattering, and the like of light in various optical equipments. Such a light control optical element normally has a high transmittance value for visible light, but it can be used for the purpose of controlling the transmittance or absorption of natural and various types of artificial light such as light control glasses.

Figure 13:
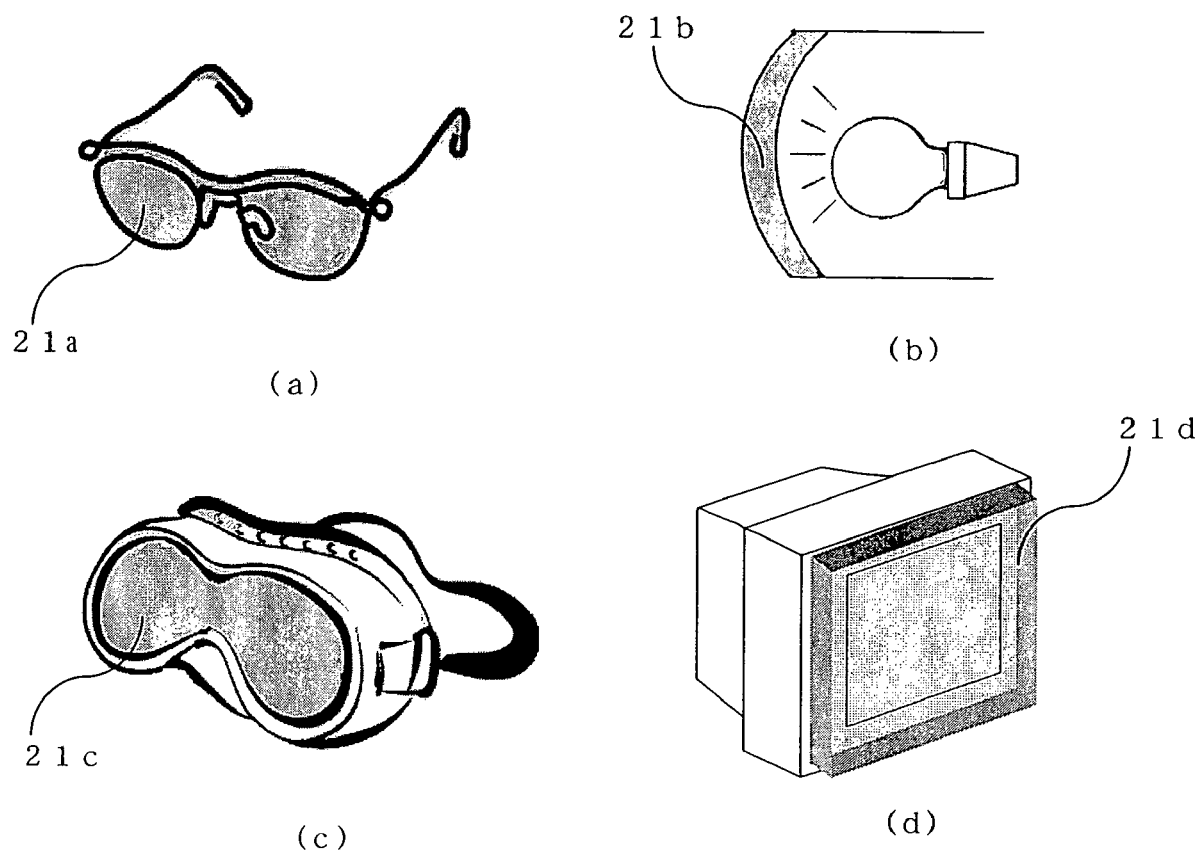
FIG. 13($a$) is a drawing showing a typical light control optical element of the present invention.
Figure 14:
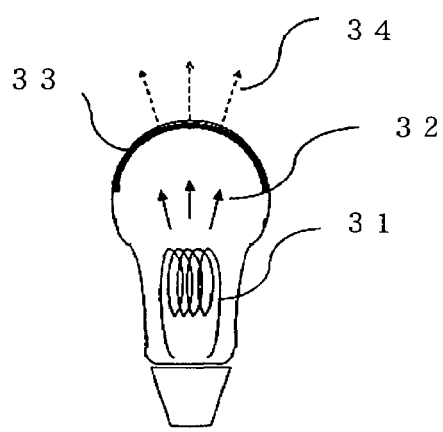
FIG. 14($a$) is a schematic drawing of a electric bulb as an example of a luminescent device.
Figure 14:
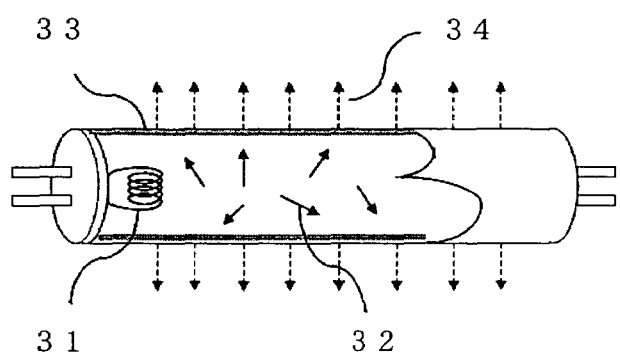
Figure 14:
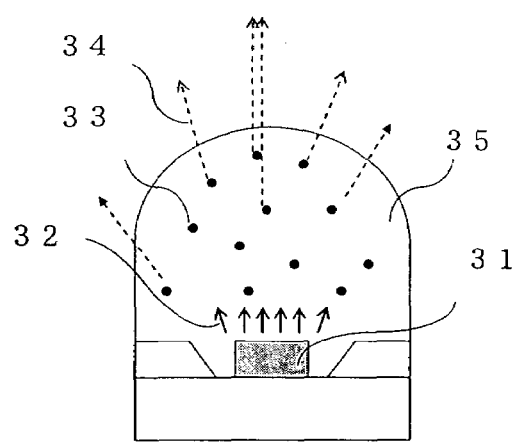

FIGS. 13(a) to 13(d) are explanatory diagrams that illustrate typical examples of the light control optical element of the present invention. In FIG. 13(a), the light control optical element is used in lenses for eyeglasses as lenses 21a. In FIG. 13(b) the light control optical element is the cover 21b used in various lighting devices (or lighting windows). FIG. 13(c) is a diagram illustrating a lens 21c (or window) used for goggles for industry such as for welding and the like, and used in medical therapy and the like. FIG. 13(d) is a diagram of an optical filter 21d wherein a light control optical element is used in a television receiver.

Among the lenses 21a for eyeglasses shown in FIG. 13(a), a sunglasses lens is the most typical example of a light control optical element that reduces the unpleasant sensation of glare by reducing the amount of intense light. More specifically, sunglasses with a strong antiglare effect can be obtained by reducing the amount of light with a wavelength of 400 to 500 nm. Another application of lenses for eyeglasses are corrective lenses for persons with a visual disorder wherein the discrimination of colors is very difficult because they congenitally have a sensitivity curve that differs from the sensitivity curve of the eyes of normal individuals, and the corrective lenses adjust the transmittance value of light to match the visual sensitivity of the person with abnormal vision by selectively increasing the absorption of light of specific wavelengths. Among the lighting windows or covers shown in FIG. 13(b), windows and covers with a strong antiglare effect can be obtained by controlling the transmittance value of light in wavelengths of approximately 560 to 600 nm for light using halogen lamps such as automobile headlights and the like.

The organic/inorganic composite containing a rare earth element or/and Period IV transition metal used in the light control optical element of the present invention is a composite of an organic polymer and a rare earth metal or/and Period IV transition metal that can be suitably used in a light control optical element that controls the transmittance value or absorption of light of a specific waveband, and concurrently controls transmission, refraction, focus, scattering and the like, and it comprises an organic polymer and an inorganic dispersion phase (rare earth metal or/and Period IV transition metal) wherein another metal is coordinated thereto via an oxygen atom(s).

As the structure of the organic/inorganic composite containing a rare earth metal or/and Period IV transition metal used in the light control optical element of the present invention, any combination may be used provided it is a composite containing a rare earth or/and Period IV transition metal, a metal capable of coordinating with the rare earth metal or/and Period IV transition metal via an oxygen atom(s), and an organic polymer. The means for forming the inorganic dispersion phase wherein the other metal coordinates with the rare earth metal or/and Period IV transition metal via an oxygen atom(s) is not particularly limited, and may be formed, for example by the reaction of a rare earth metal salt and a metal alkoxide.

The composite of the organic polymer and the inorganic dispersion phase wherein coordination of the rare earth metal or/and Period IV transition metal with the other metal occurs via an oxygen atom(s) can, for example, be prepared by mixing the inorganic dispersion phase formed by the reaction of the aforementioned metal alkoxide and the rare earth metal salt or/and Period IV transition metal salt together with the organic polymer and dispersing the same therein.

EXAMPLE 13

<Preparation of the Organic Dispersion Phase>

Neodymium acetate that had been dehydrated under vacuum for 1 hour at 110° C. and tri-s-butoxy aluminum were added together in propylene glycol α-monomethyl ether (Nd/Al=3 molar, mathematically converted concentration of total oxides of Nd and Al 5 mass %) and refluxed for 1 hour to obtain a light purple transparent liquid. The particle size of the reaction product obtained thereby was measured using dynamic light scattering, and it was confirmed that the reaction product comprised composite nanoparticles with a peak top of 2.3 nm in diameter. In addition, coordination of the Al via an oxygen atom(s) with the Nd was verified before and after the reaction with tri-s-butoxy aluminum by the change in 27Al-NMR spectrum.

<Preparation of Composite of Inorganic Dispersion Phase and Transparent Organic Polymer>

Hydroxypropyl cellulose (Nippon Soda Co., Ltd.) was used as the transparent organic polymer. This organic polymer and the composite nanoparticles containing NdAl prepared according to the above method were mixed together in Ethyl Cellosolve, and stirred for 2 hours at room temperature to obtain a liquid mixture. The mixture ratio was controlled so that the neodymium (Nd) content is 8% in mass in terms of solid content of the composite.

The liquid mixture formulated as noted above was poured into a polytetrafluoroethylene container used as mold, and an approximately 1 mm thick cast molded product of the organic/inorganic composite containing Nd was obtained by evaporating the Ethyl Cellosolve at 120° C. and drying.

<Measurement of Spectroscopic Absorption Properties>

The spectroscopic absorption properties of the organic/inorganic composite containing Nd obtained thereby was measured using a spectrophotometer. FIG. 3 shows the spectroscopic absorption spectrum of the composite nanoparticles containing Nd—Al/hydroxypropyl cellulose composite prepared according to the above method. It is clear that absorption in the wavebands of approximately 500 to 540 nm and approximately 560 to 600 nm originating from the Nd absorption can be assured in the composite nanoparticles containing Nd—Al/hydroxypropyl cellulose composite.

<Fabrication of a Window for Lighting>

In accordance with the aforementioned method of preparing the organic/inorganic composite containing Nd, a coating layer of the organic/inorganic composite containing Nd was formed on the cover for a halogen lamp that is widely used. It was confirmed that when this cover was used, the glare specific to halogen lamps was reduced, and such a cover will be effective as an automobile headlight and the like.

EXAMPLE 14

<Preparation of the Inorganic Dispersion Phase>

Praseodymium acetate that had been dehydrated for 1 hour at 110° C. and tri-s-butoxy aluminum were added together in propylene glycol-α-monomethyl ether (Pr/Al=3 molar, mathematically converted concentration of total oxides of Pr and Al 5 mass %) and refluxed for 1 hour to obtain a light green transparent liquid. The particle size of the reaction product obtained thereby was measured using dynamic light scattering, and it was confirmed that the reaction product comprised composite nanoparticles with a peak top of 6.5 nm in diameter. In addition, coordination of the Al via an oxygen atom(s) with the Pr was verified before and after the reaction with tri-s-butoxy aluminum by the change in 27Al-NMR spectrum.

<Preparation of Composite of Inorganic Dispersion Phase and Transparent Organic Polymer>

A photopolymerizable acrylic resin "Cyclomer" (Daicel Chemical Industries, Ltd.) was used as the transparent organic polymer. This organic polymer, the composite nanoparticles containing PrAl prepared according to the above method, and a photoradical initiator. "Irgacure 369" (Ciba Specialty Chemicals) were mixed together in PGMEA, and stirred for 2 hours at room temperature to obtain a liquid mixture. The mixture ratio was controlled so that the praseodymium (Pr) content is 10% in mass in terms of solid content of the composite.

Using a polytetrafluoroethylene container as a mold, an approximately 1 mm thick transparent cast molded product of the organic/inorganic composite containing Pr was obtained by evaporating the PGMEA at 120° C. and drying.

<Measurement of Spectroscopic Absorption Properties>

The spectroscopic absorption properties of the organic/inorganic composite containing Pr obtained thereby was measured using a spectrophotometer. The spectroscopic absorption spectrum of the composite nanoparticles containing Pr—Al/photopolymerizable acrylic resin composite prepared according to the above method was the same as that of FIG. 9 shown in EXAMPLE 10. It is clear that absorption in the wavebands of approximately 440 to 490 nm originating from the Pr absorption can be assured in the composite nanoparticles containing Ni—Nb/photopolymerizable acrylic resin composite.

<Preparation of Lens>

A lens was prepared in accordance with the method for preparing the aforementioned organic/inorganic composite containing Pr. It was confirmed that this lens is suitable as an antiglare lens because the absorption thereby of blue-green light components is selectively high.

EXAMPLE 15

<Preparation of the Inorganic Dispersion Phase>

Nickel acetate that had been dehydrated for 1 hour under vacuum at 100° C. and pentaethoxy niobium were added together in ethylene glycol monomethyl ether (Ni/Nb=2 molar, mathematically converted concentration of total oxides of Ni and Nb 5 mass %) and refluxed for 1 hour to obtain a green transparent liquid. The particle size of the reaction product obtained thereby was measured using dynamic light scattering, and it was confirmed that the reaction product comprised composite nanoparticles with a peak top of 2.9 nm in diameter.

<Preparation of Composite of Inorganic Dispersion Phase and Transparent Organic Polymer>

The photopolymerizable resin "Cyclomer" ((Daicel Chemical Industries, Ltd.) was used as the transparent organic polymer in accordance with EXAMPLE 2. This organic polymer and the composite nanoparticles containing Ni—Nb prepared according to the above method were mixed together in Ethyl Cellosolve, and stirred for 2 hours at room temperature to obtain a liquid mixture. The mixture ratio was controlled so that the Ni content is 8% in mass in terms of solid content of the composite.

The liquid mixture formulated as noted above was poured into a polytetrafluoroethylene container used as mold, and an approximately 1 mm thick transparent cast molded product of the organic/inorganic composite containing Nb was obtained by evaporating the Ethyl Cellosolve at 120° C. and drying.

<Measurement of Spectroscopic Transmittance Value>

The spectroscopic absorption properties of the organic/inorganic composite containing Ni obtained thereby was measured using a spectrophotometer. The spectroscopic absorption spectrum of the composite nanoparticles containing the Ni—Nb/hydroxypropyl cellulose composite prepared according to the above method was the same as that of FIG. 10 shown in EXAMPLE 11. It is clear that absorption in the wavebands of approximately 900 to 600 nm and approximately 450 nm or less originating from the Ni absorption can be assured in the composite nanoparticles containing Ni—Nb/hydroxypropyl cellulose composite.

Based on the above results the present invention makes it possible to provide an organic/inorganic composite wherein a rare earth metal or/and Period IV transition metal is doped at a high concentration in an organic polymer, and the original absorption properties of the doping elements can be expressed thereby.

<Preparation of Lens>

A lens was prepared in accordance with the method for preparing the aforementioned organic/inorganic composite containing Ni. It was confirmed that this lens is suitable as an antiglare lens because the absorption thereby of blue-green to UV light components is selectively high.

The present invention can be used in a light control optical element that is used for controlling the transmittance and absorption of light of a specific wavelength or waveband, and it can assume many advantageous forms in accordance with the needs thereof.

A light control lens can be listed as an example thereof. More specific examples of applications include sunglasses, antiglare lenses, lenses for persons with visual abnormalities, goggles for industrial welding (protective eyeglasses), goggles used in medical therapy and the like.

Enclosures for various light sources, window materials and the like can also be listed as applications of the present invention. More specific examples include window material for automobile headlights and various point light sources, and lens cover materials and the like.

With respect to lighting such as various EDT lights and reflector lamps and the like that are widely used in general households, the present invention can be used to control the spectrum of the lamplight extracted by applying the present invention to decorative windows and the like. For example, it is possible to control color rendering by attenuating the blue components in a white fluorescent light to create a warm color tone and the like.

The present invention can be applied as a material for industrial windows and building windows having a filter effect using transparent polymer material, or as a display filter for television and the like. For example, by doping with a rare earth metal such as neodymium that selectively absorbs light in the red band, the present invention can become a window material having a heat ray attenuating effect.

The luminescent device of the present invention is equipped with a light emitting element and a rare earth luminescence material. The rare earth luminescence material can be any combination provided it is a composite comprising a rare earth metal, a metal capable of coordinating with the rare earth metal via an oxygen atom(s), and an organic polymer.

The means of forming the organic dispersion phase wherein another metal coordinates with the rare earth metal via an oxygen atom(s) is not particularly limited and for example, the organic dispersion phase may be formed by the reaction of a rare earth metal salt and a metal alkoxide.

The composite of the organic polymer and the inorganic dispersion phase wherein coordination of the rare earth metal with the other metal occurs via an oxygen atom(s) can, for example, be prepared by mixing the inorganic dispersion phase formed by the reaction of the aforementioned metal alkoxide and the rare earth metal salt together with the organic polymer and dispersing the same therein.

[Light Emitting Element]

Items generally called electric bulbs, EDT fluorescent lamps, LEDs and the like can be used as the light emitting element.

Examples of electric bulbs include not only incandescent bulbs wherein electric current flows through a filament to heat it, and then light is discharged as thermal radiation, but also krypton lamps wherein krypton gas is sealed within the electric bulb, halogen lamps that utilize the halogen cycle, and the like.

Examples of EDT fluorescent lamps include not only the most general fluorescent lamp using mercury discharge, but also black lights that emit only UV light in the same manner.

High intensity discharge lamps (HID lamps) are also items that emit fluorescent light by the collision of electrons generated from an electrode similar to that in an EDT fluorescent lamp and mercury vapor sealed in the lamp, but because the density of mercury atoms during ignition and the temperature are much higher than in a conventional fluorescent lamp, they are often classified separately from fluorescent lamps. As a group of these HID lamps, sodium lamps, metal halide lamps, mercury lamps, and the like can be used as the light emitting element in the present invention.

LEDs are light emitting elements utilizing various semiconductors, and obtained by forming pn junctions. Known examples of semiconductors include gallium-arsenide, gallium phosphide, aluminum-gallium-indium-fluorescent materials, indium-gallium-arsenic-fluorescent materials, zinc selenide, zinc sulfide, indium sulfide, zinc-sulfur-selenium, gallium nitride, indium-gallium-nitrogen, silicon carbide, and the like but are by no means limited to the same. Semiconductor lasers wherein these semiconductors are formed into a structure capable of laser excitation can be sued as the light emitting element of the present invention.

Examples of light emitting elements that can be used in the present invention have been presented above, but the light emitting element of the present invention is not particularly limited provided it is one that can convert electric energy to light energy.

[Rare Earth Metal Luminescence Material]

The term rare earth metal luminescence material refers to rare earth metal atoms alone, or a rare earth metal complex or molecular cluster containing a rare earth metal wherein a specific molecule or group of molecules is coordinated thereto for the purpose of increasing the stability and solubility/dispersibility of the rare earth metal atoms.

Luminescence material that is generally used is one wherein a target substance is attached by a method such as sputtering in which a bulk body is initially formed, said bulk body being one in which a rare earth metal is doped into transparent oxide crystals such as $Y_3Al_5O_{12}$ (YAG), $YLiF_4$ (YLF), $YVO_4$, and the like, or into glass such as silicate glass, phosphate glass, fluoride glass, and the like during the crystal growing process or glass forming process, and then the bulk body is pulverized and kneaded into an organic material, and the bulk body is used as a target for sputtering. Recently, a method for obtaining fine particles without pulverization has been adopted wherein doping of the rare earth metal is performed during the growth process of the aforementioned transparent crystals of nanometer size by a sol-gel process and the like.

In any event, with respect to the problem of doping a rare earth metal into an organic medium which is the object of this application, in order to distinguish prior art methods wherein the rare earth metal is temporarily supported on a material that can easily incorporate a rare earth metal such as the aforementioned transparent crystals or glass and the like, and then kneaded into an organic medium, from a process wherein a rare earth complex or a molecular cluster containing a rare earth metal in which another molecule or group of molecules is coordinated to the rare earth metal is doped directly into the organic medium, the former shall be defined as a fluorescent material, and the latter as a rare earth metal luminescence material.

EXAMPLE 16

<Preparation of Composite of Inorganic Dispersion Phase>and Transparent Organic Polymer The Eu—Al luminescence material, Tb—Al luminescence material, and Ce—Al luminescence material prepared in EXAMPLE 3, 5, and 8, respectively were mixed in Ethyl Cellosolve and stirred for 2 hours to obtain a liquid mixture. The mixture ratio was controlled so that the respective ratios of Eu, Tb, and Ce in the composite nanoparticles would be 5% of the total solids.

The liquid mixture formulated as noted above was poured into a polytetrafluoroethylene container used as mold while evaporating and drying the Ethyl Cellosolve at 120° C. or less, and an approximately 1 mm thick cast molded product of the organic/inorganic composite containing Eu, Tb, and Ce was prepared on a glass panel.

<Preparation of Luminescent Device>

Figure 15:
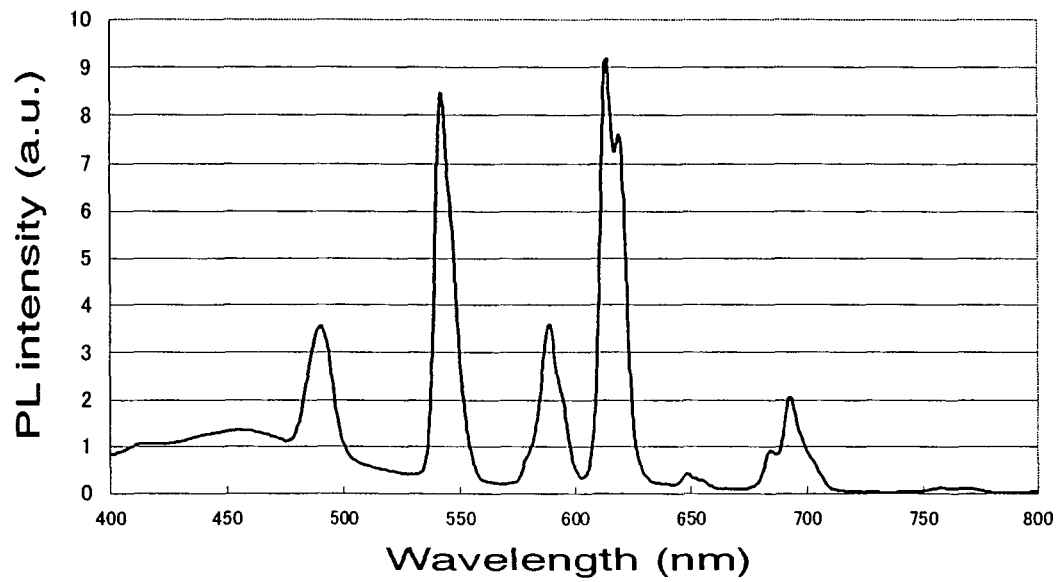
FIG. 15 is a photoluminescence spectrum in accordance with the mixed emission from the Eu—Al fluorescent material, the Tb—Al fluorescent material, and the Ce—Al fluorescent material used in Example 4 among the luminescent devices of the present invention.
Figure 16:
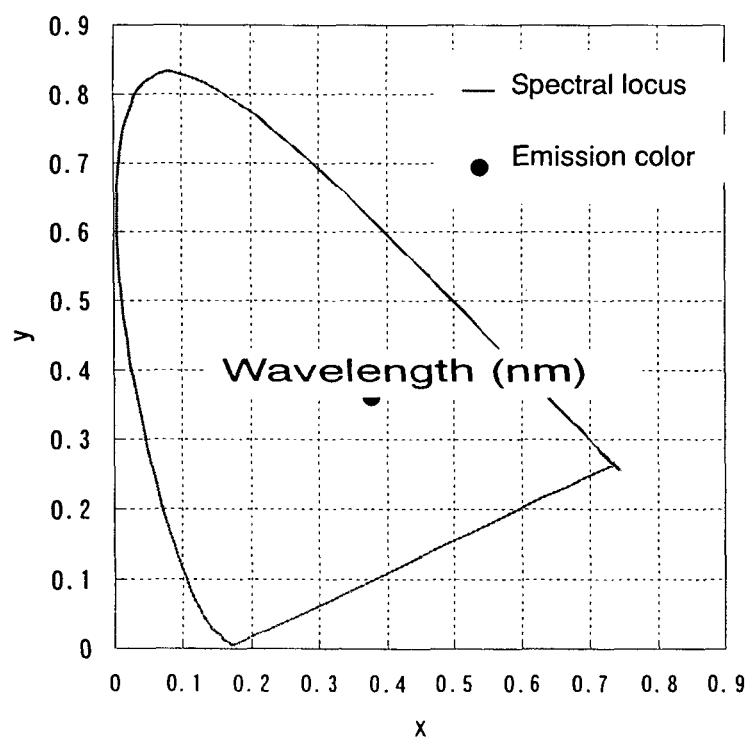
FIG. 16 is a chromaticity diagram concerning the mixed emission from the Eu—Al fluorescent material, the Tb—Al fluorescent material and the Ce—Al fluorescent material used in Example 4 among the luminescent devices of the present invention.

An LED emitting UV light at a wavelength of 380 nm was mounted on a printed board as a light emitting element, and connected to a 6 V DC power source via a 330Ω resistance to prepare a light emitting unit. After this light emitting unit was enclosed in an aluminum enclosure, and the cast molded products of the organic/inorganic composite containing the Eu—Al luminescence material, Tb—Al luminescence material, and Ce—Al luminescence material prepared in the above manner were fitted to form a window. Thereby a luminescent device using the UV light LED as a light emitting element, and having a window wherein the cast molded product of the organic/inorganic composite containing Eu—Al, Tb—Al, and Ce—Al was formed on glass plate. When current was applied to this luminescent device, white light was observed. In addition when the emitted color was measured with a spectroscope, an emission spectrum such as that shown in FIG. 15 was obtained. When a CIE chromaticity diagram was prepared using the emission spectrum shown in FIG. 15, a chromaticity diagram such as that shown in FIG. 16 was obtained. It was confirmed that the emitted color of these Examples represented by the color display chart was white, and this device was effective as a white light emitting element.

The present invention is suitably used in a luminescent device wherein electric energy is converted to light energy.

Examples of such a luminescence device include LED elements of various colors, and lighting devices utilizing the same. It is known that by selecting the material of the semiconductor various emission colors can be obtained in the LED per se, but depending on the field of use, different color rendering properties are needed. For example, in a white LED obtained by exciting a YAG fluorescent material by a blue LED, the overall paleness stands out. There is a problem when such a luminescence device is used for lighting in medical therapy because it cannot be accurately determined whether the color of blood is normal or not. The above problem can be solved in such a case by doping an LED sealing resin with the composite nanoparticles containing Eu—Al obtained in the present invention, which will not only attenuate the paleness by the accompanying Eu absorption, but also add light emission in the red band from Eu.

In addition, such an LED can be used in a modular, large flat display device. More specifically, there has not been an LED in such a display that emits suitable green light in the past, and the display could not perform sufficiently as an RGB color display. However, the above problem can be solved by doping a UV LED sealing resin with composite nanoparticles containing Tb—Al obtained in the present invention, and a green LED with superb color emitting properties can be obtained thereby.

The Invention claimed is:

1. An organic/inorganic composite comprising:
    at least one first metal selected from the group consisting of rare earth metals and Period IV transition metals being dispersed in an organic polymer, and
    an inorganic dispersion phase including at least one second metal other than the at least one first metal, the at least one second metal being coordinated to the at least one first metal via oxygen.

2. The organic/inorganic composite according to claim 1, wherein the inorganic dispersion phase has an average particle diameter of 0.1 to 1000 nm.

3. The organic/inorganic composite according to claim 1, wherein a proportion of the at least one first metal is 90 mass % or less, as calculated in terms of solid content based on a total mass of the organic polymer and the inorganic dispersion phase in which the at least one second metal is coordinated to the at least one first metal via oxygen.

4. The organic/inorganic composite according to claim 1, wherein the at least one second metal oxygen is one or more members selected from Group 3B, Group 4A, and Group 5A metals.

5. The organic/inorganic composite according to claim 1, wherein the inorganic dispersion phase comprising the at least one first metal and the at least one second metal coordinated thereto via oxygen is prepared from a salt of the at least one rare first metal and an alkoxide of the at least one second metal.

6. An optical amplifier having an optical waveguide for transmitting light of a specific wavelength or waveband (signal light) and light having a different wavelength or waveband therefrom (excitation light), in which intensity of the signal light is amplified by the excitation light,
    wherein the optical waveguide is an organic/inorganic composite comprising:
        at least one first metal selected from the group consisting of rare earth metals and Period IV transition metals being dispersed in an organic polymer, and
        an inorganic dispersion phase including at least one second metal other than the at least one first metal, the at least one second metal being coordinated to the at least one first metal via oxygen.

7. A light control optical element comprising the an organic/inorganic composite, wherein the organic/inorganic composite comprises:
    at least one first metal selected from the group consisting of rare earth metals and Period IV transition metals being dispersed in an organic polymer, and
    an inorganic dispersion phase including at least one second metal other than the at least one first metal, the at least one second metal being coordinated to the at least one first metal via oxygen.

8. A luminescent device comprising a light emitting element and an organic/inorganic composite in which a rare earth metal luminescence material emitting light when excited by light generated by the light emitting element is dispersed in an organic polymer, the organic/inorganic composite comprising:
    at least one first metal selected from the group consisting of rare earth metals and Period IV transition metals being dispersed in an organic polymer, and
    an inorganic dispersion phase including at least one second metal other than the at least one first metal, the at least one second metal being coordinated to the at least one first metal via oxygen.

* * * * *